(12) United States Patent
Coppock

(10) Patent No.: US 11,613,746 B2
(45) Date of Patent: Mar. 28, 2023

(54) METHODS FOR DEVELOPING VIRUS PROTEIN SPECIFIC CAPTURE AGENTS, CAPTURE AGENTS, AND METHODS OF USING THE CAPTURE AGENTS

(71) Applicant: U.S. Army Research Laboratory, Adelphi, MD (US)

(72) Inventor: Matthew B. Coppock, Arlington, VA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 188 days.

(21) Appl. No.: 16/407,780

(22) Filed: May 9, 2019

(65) Prior Publication Data
US 2020/0354713 A1    Nov. 12, 2020

(51) Int. Cl.
*C12N 15/10* (2006.01)
*G01N 33/543* (2006.01)
(Continued)

(52) U.S. Cl.
CPC ..... *C12N 15/1065* (2013.01); *C12N 15/1072* (2013.01); *C12N 15/1086* (2013.01);
(Continued)

(58) Field of Classification Search
CPC ............ C12N 15/1065; C12N 15/1072; C12N 15/1086; C40B 40/02; C40B 40/10;
(Continued)

(56) References Cited

U.S. PATENT DOCUMENTS 8,449,887 B2    5/2013   Brehin et al.
9,738,704 B2    8/2017   Warier et al.
(Continued)

FOREIGN PATENT DOCUMENTS

WO       2012078116 A1    6/2012
WO    WO-2014205317 A2 * 12/2014    ............. C07K 1/047
WO       2015010125 A1    1/2015

OTHER PUBLICATIONS

Storz et al. (Annual Review of Biochemistry, 2014, 83:753-777) (Year: 2014).*

(Continued)

*Primary Examiner* — Jeremy C Flinders
(74) *Attorney, Agent, or Firm* — Eric B. Compton

(57) ABSTRACT

A method for developing capture agents for target proteins employs a compound library to find cyclic peptide sequences that bind the target protein. The target protein is also reacted with a clickable group-provider reagent to provide the protein with clickable groups. The compounds in the library are provided with complementary clickable groups that bind the clickable group on the target protein when the peptide sequences bind the target protein. In some embodiments, the cyclic peptide sequences that bind the target protein are incorporated into constructs having one or more arms that can serve as capture agents or potential treatments against the pathogens from which the target protein is derived. Some embodiments provide pharmaceutical compositions for immunoassays, diagnostics, therapeutics or the like, that employ the constructs.

26 Claims, 12 Drawing Sheets

Specification includes a Sequence Listing.

(51) Int. Cl.
  *C40B 40/10* (2006.01)
  *G01N 33/50* (2006.01)
  *C40B 40/02* (2006.01)
  *G01N 33/68* (2006.01)

(52) U.S. Cl.
  CPC .............. *C40B 40/02* (2013.01); *C40B 40/10* (2013.01); *G01N 33/5008* (2013.01); *G01N 33/543* (2013.01); *G01N 33/6845* (2013.01)

(58) Field of Classification Search
  CPC ............ G01N 33/5008; G01N 33/532; G01N 33/33543; G01N 33/6845
  See application file for complete search history.

(56) References Cited

U.S. PATENT DOCUMENTS

| | | |
|---|---|---|
| 9,902,765 B2 | 2/2018 | Doranz et al. |
| 2010/0105089 A1 | 4/2010 | Sooter |
| 2015/0078999 A1 | 3/2015 | Heath et al. |
| 2017/0349754 A1 | 12/2017 | Coppock |

OTHER PUBLICATIONS

Das, S., et al., "A General Synthetic Approach for Designing Epitope Targeted Macrocyclic Peptide Ligands," Angew Chem Int Ed Engl. Nov. 2, 2015; 54(45), pp. 1-11.

Coppock, M., et al., "Protein catalyzed capture agents with tailored performance for in vitro and in vivo applications," Peptide Science 108(2), Aug. 2016, pp. 1-13.

Vashist, S., et al., "Handbook of Immunoassay Technologies," Academic Press, 1st Edition, Jan. 4, 2018, Table of Contents.

Coppock, M., et al., "A novel discovery, maturation, and assay integration approach for the development of ruggedized multivalent capture receptors exemplified against the chikungunya virus E2 protein," Sensing and Bio-Sensing Research 22 (2019), 100248, pp. 1-8 (available online Nov. 27, 2018).

Coppock, M., et al., "A universal method for the functionalization of dyed magnetic microspheres with peptides," Methods 158 (2019), Jan. 30, 2019, pp. 12-16. (availabe online Jan. 30, 2019).

Das et al., "A General Synthetic Approach for Designing Epitope Targeted Macrocyclic Peptide Ligands," Angew. Chem.Int.Ed. 2015,54,13219-13224.

Lai et al., "Epitope-targeted Macrocyclic Peptide Ligand with Picomolar Cooperative Binding to Interleukin-17F," Chem. Eur. J. 2018, 24, 3760-3767.

Liang et al., "Inhibition of Heme Sequestration of Histidine-Rich Protein 2 Using Multiple Epitope-Targeted Peptides," J. Pep Sci. 2019;25e3203.

Idso et al., "Antibody-Recruiting Protein-Catalyzed Capture Agents to Combat Antibiotic-Resistant Bacteria," Chem. Sci., 2020, 11,3054.

Sarkar, et al., "Inhibiting Matrix Metalloproteinase-2 Activation by Perturbing Protein-Protein Interactions Using a Cyclic Peptide." J Med Chem. Jul. 9, 2020; 63(13): 6979-6990.

Narayanam, et al., "Positron Emission Tomography Traer Design of Targeted Synthetic Peptides via 18F-Syndone Alkyne Cycloaddition," Bioconjugate Chem. 2021, 32, 2073-2082.

Shuker et al., "Discovering High-Affinity Ligands for Proteins: SAR by NMR," Science 274: 1531 (1996).

Erlanson et al., "Site-directed ligand discovery," Proc. Natl. Acad. Sci. USA 97:9367 (2000).

* cited by examiner

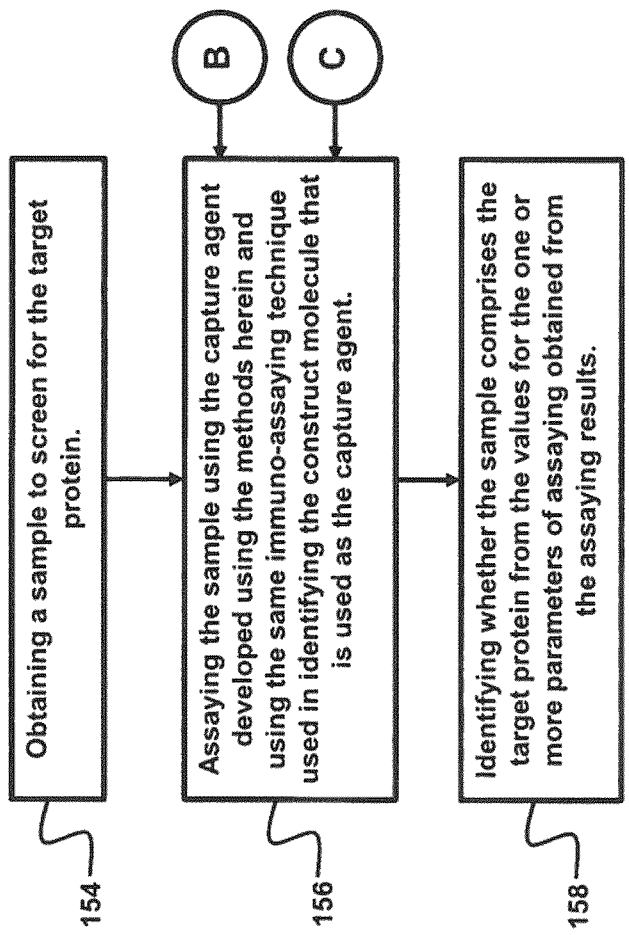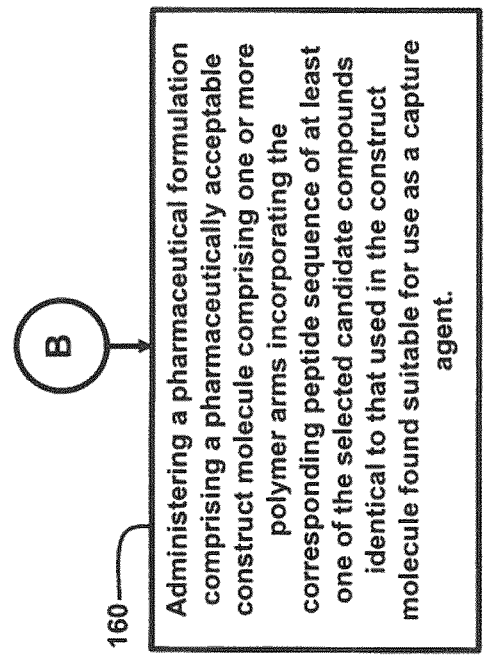

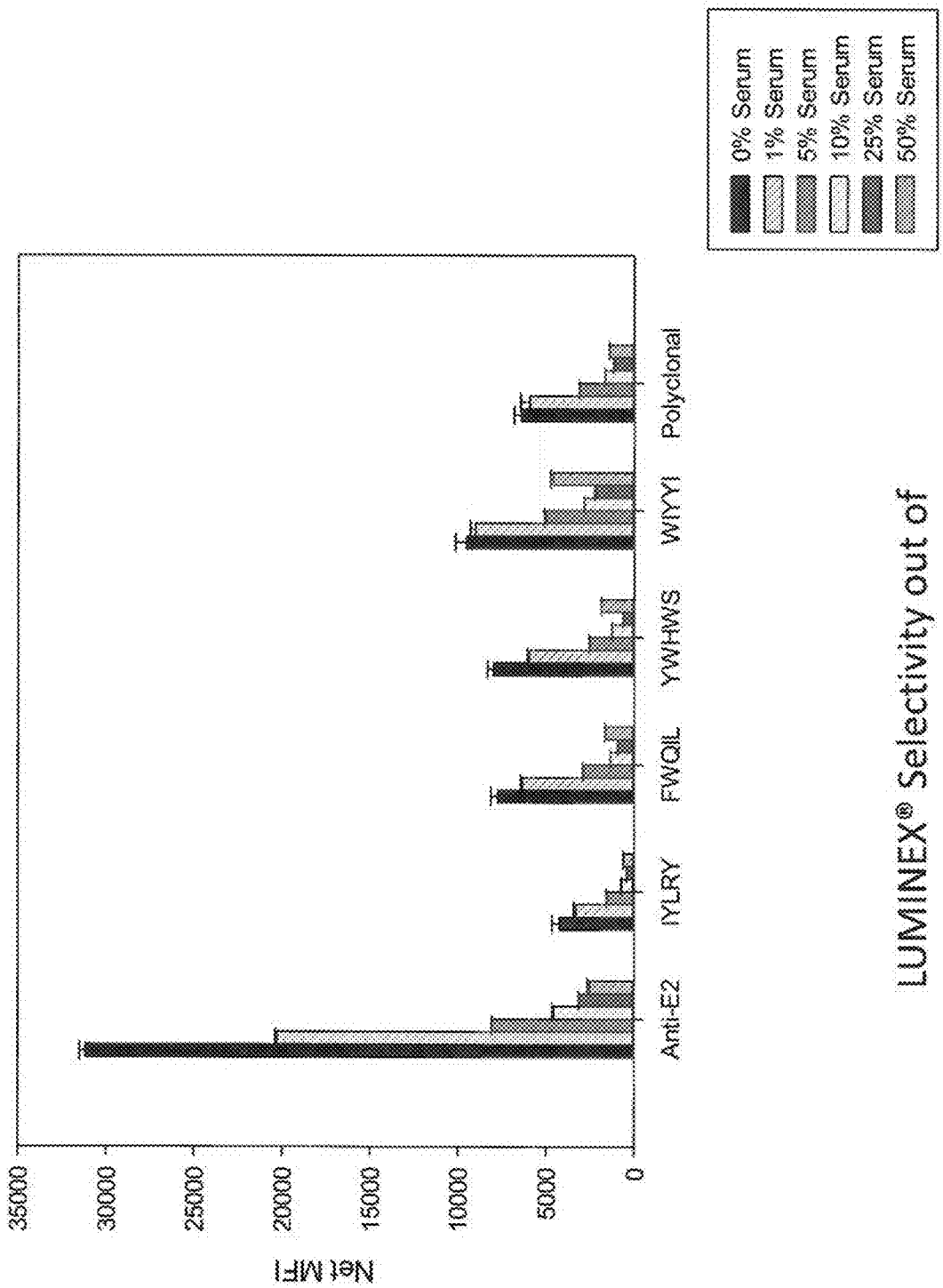

METHODS FOR DEVELOPING VIRUS PROTEIN SPECIFIC CAPTURE AGENTS, CAPTURE AGENTS, AND METHODS OF USING THE CAPTURE AGENTS

GOVERNMENT INTEREST

The embodiments herein may be manufactured, used, and/or licensed by or for the United States Government without the payment of royalties thereon.

BACKGROUND

Technical Field

The embodiments herein generally relate to methods for developing synthetic capture agents for target proteins, synthetic capture agents, and compositions of such synthetic capture agents, which have applications in pathogen detection, diagnostics, and potential therapeutic uses. Some embodiments herein relate, in particular, to a method for developing synthetic capture agents, synthetic capture agents, and compositions of such capture agents for the Chikungunya virus (CHIKV) E2 surface protein for assays, therapeutics, or the like.

Description of the Related Art

Within this application there are several patents and publications that are referenced. The disclosures of all these patents and publications, in their entireties, are hereby expressly incorporated by reference into the present application.

The Chikungunya virus (CHIKV) is a pathogen that causes the disease Chikungunya. Symptoms of the disease include fever, joint pain, headache, muscle pain, joint swelling, and a rash. Accordingly, the Chikungunya virus is a public health concern. Furthermore, Alphaviruses, such as CHIKV, are recognized as a significant threat to both national security and public health. Although natural infection in the United States is relatively low, Alphaviruses have been the subject of significant interest in historical biological weapon development programs due their high infectivity when aerosolized, ease of large scale production, stability under a wide range of environmental conditions, and proven tractability to genetic manipulation. Accordingly, there have been past attempts to develop a detection agent for CHIKV.

U.S. Pat. No. 8,449,887 B2, issued to Anne-Claire Brehin, et al. on May 28, 2013, U.S. Pat. No. 9,738,704 B2, issued to Lucile Warter, et al. on Aug. 22, 2017, International Publication No. WO 2012/078116 A1, by Joo Chuan Tong, et al., published on Jun. 14, 2012, and International Publication No. WO 2015/010125 A1, by Benjamin Doranz, et al., published on Jan. 22, 2015 all relate to the development of molecules for CHIKV E2 binding. While all of these patents describe reagents developed against CHIKV E2, none are cyclic peptide-based.

United States Patent Application Publication No. US 2015/0078999 A1, by James R. Heath, et al., published on Mar. 19, 2015, relates to a cyclic peptide library. However, it does not show azide-functionalized cyclic peptide library compounds or the application of such a library to the whole protein among other differences.

There are currently no approved antivirals or vaccines available to the general population in the United States of America for CHIKV infection. Therefore, there is a need to develop diagnostic, detection, and therapeutic compounds and compositions to combat CHIKV infection and many other diseases and biological threats.

SUMMARY

In view of the foregoing, an embodiment herein provides a method for the rapid screening of full protein targets for the development of peptide-based reagents used as highly stable biodetection receptors for point-of-need sensing and diagnostics, as well as therapeutic measures. As an example application, the method was performed against the Chikungunya virus E2 protein, the virus being a high priority target from the viewpoint of national security and safety of armed services personnel, resulting in four unique cyclic peptide sequences specific to the CHIKV E2 protein. The individual peptides were then matured into constructs having one or more arms, many of which outperformed a commercially available antibody raised against CHIKV E2. In example embodiments, 3-arm constructs resulted in over 2 orders of magnitude affinity improvement and greatly improved target selectivity compared to 1-arm constructs.

Some embodiments herein provide methods for rapid multi-capture agent development. The screening method of some embodiments herein functionalize the protein target with alkynes and use an azide-functionalized cyclic peptide library for the screening process. Other screening processes with these cyclic peptides either do not functionalize the protein (which usually results in weaker binders), require another molecule to have already been discovered against the target to build off of, or require structural information about the protein.

The sequences (WIYYI (SEQ ID NO: 1), YWHWS (SEQ ID NO: 2), IYLRY (SEQ ID NO: 3), FWQIL (SEQ ID NO: 4)) down-selected from the screen are unique binders to CHIKV E2. Typical E2 binders are mainly monoclonal or polyclonal antibodies, which are large proteins, and not such relatively small peptides.

The embodiments herein include constructs having one or more arms that can be used as part of pharmaceutical formulations that are useful for biological threat detection and medical diagnostics and are potentially useful as medicinal therapeutics for CHIKV and other types of infectious diseases. The constructs may be of each down-selected peptide or may employ a mix of the plurality of the down-selected peptides, and the multi-arm constructs exhibit improved affinity and selectivity for the target protein.

BRIEF DESCRIPTION OF THE DRAWINGS

The embodiments herein will be better understood from the following detailed description with reference to the drawings, in which:

FIGS. 6A-6C are a flow diagram illustrating an embodiment of the method disclosed herein for developing a capture agent for a target protein;

FIG. 6D is a flow diagram illustrating an embodiment of the method disclosed herein for detecting a target protein using a capture agent for the target protein;

FIGS. 8A-8B illustrate bar graphs showing results indicative of LUMINEX® Selectivity of 1-Arm and 3-Arm constructs as a function of the presence of increasing concentrations of human serum.

DETAILED DESCRIPTION

Figure 1:
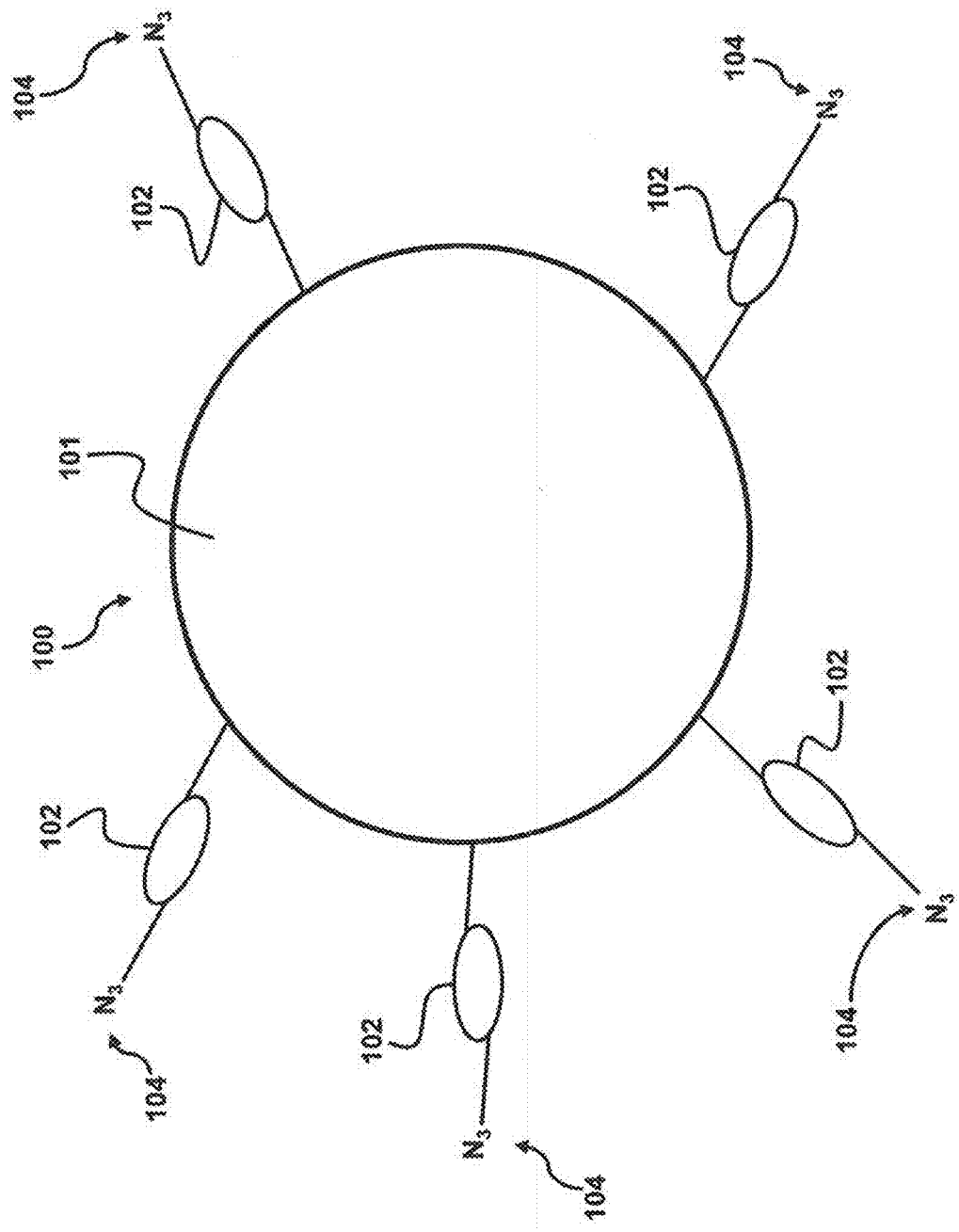
FIG. 1 illustrates schematically an embodiment of the library compound and solid support disclosed herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The term "pharmaceutically acceptable" as used herein in reference to an item means that the item is, within the scope of sound medical judgment, suitable for use in contact with the tissues of humans and lower animals without undue toxicity, irritation, allergic response, and the like, commensurate with a reasonable benefit/risk ratio, and effective for its intended use. When used in reference to items other than the primary, active drug or pharmaceutical agent, "pharmaceutically acceptable" also means that, within the scope of sound medical judgment and commensurate with a reasonable benefit/risk ratio, the item will not unduly impair the effectiveness of the primary, active drug or pharmaceutical agent for its intended use.

Referring to FIGS. 1-5 and 7, some embodiments herein relate to a method (110) for developing a capture agent for a target protein 117. In one embodiment, the method (110) comprises providing (112) the target protein; reacting (114) the target protein with at least one click handle moiety precursor, examples of which are provided below, to provide a synthetic antigen composition comprising at least one synthetic antigen 121 that comprises at least one click handle moiety 119 (examples of click handle moieties are also provided below); providing (116) a compound library of compounds that each have a complementary click handle that is capable of binding the click handle moiety 119 of the synthetic antigen 121, each of the compounds having at least one variable portion comprising at least one corresponding peptide sequence; incubating (118) the synthetic antigen composition together with at least a portion the compound library; labeling (120) the synthetic antigen to allow detection of library compounds having synthetic antigen bound thereto. That is to say the detection occurs after the step of incubating and not necessarily after the labeling step. The labeling step may occur before or after the incubating step (118) unless otherwise specified. The method (110) further comprises selecting (122) one or more compounds from the compound library wherein each compound selected binds to the synthetic antigen in such a way that the complementary click handle of the compound will simultaneously bind the click handle moiety 119 of the synthetic antigen 121; and sequencing (124) each compound selected to obtain the corresponding peptide sequence of each compound selected, wherein each compound selected is capable of being used as a capture agent or for incorporation into a capture agent for the target protein.

Examples of click handle moiety precursors include, but are not limited to, propargyl-N-hydroxysuccinimidyl ester, amine-$(PEG)_n$-azide, amine-alkyl-azide, amino acid-$(PEG)_n$-azide, amino acid-alkyl-azide, carboxyl-$(PEG)_n$-azide, and carboxyl-alkyl-azide. Examples of click handle moieties include, but are not limited to, alkyne groups such as the propargyl group (also known as an acetylene group) and the azide group.

Figure 2:
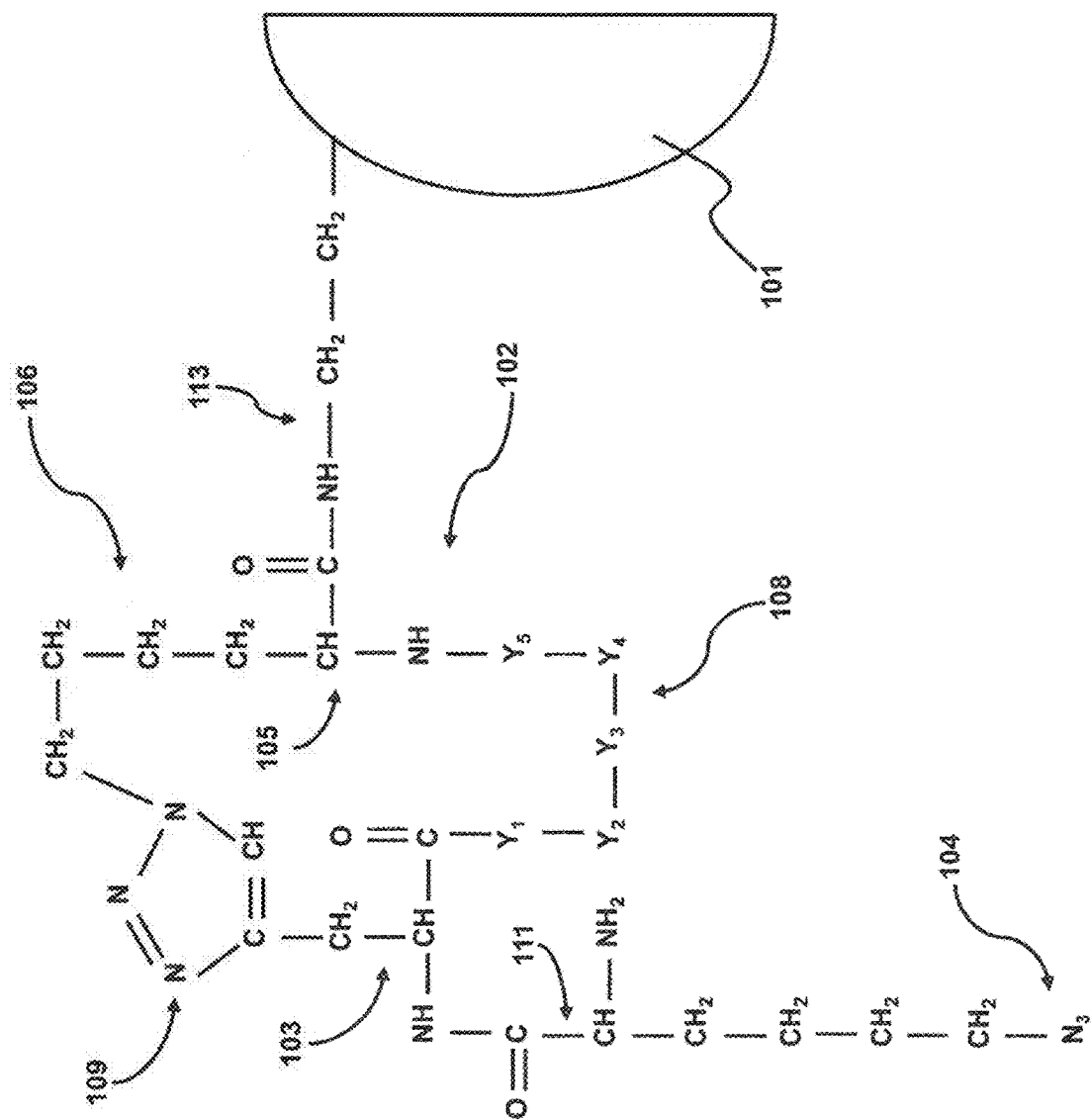
FIG. 2 is an enlarged schematic illustration of the embodiment of the library compound and solid support of FIG. 1 showing the chemical structure of the library compound.

In the embodiments herein, the synthetic antigen 121 comprises a modified version of the target protein 117 that is modified by at least incorporating the at least one click handle moiety 119. In the illustrated example, the click handle moiety 119 is an acetylene or propargyl group (—C≡CH) or another suitable alkyne. The compound library may be a cyclic peptide library of cyclic peptides as illustrated in FIG. 2. In some examples, the synthetic antigen is not subjected to a pegylation reaction and is not a pegylation product. In some examples, the target protein may be a whole protein so that the method does not require any knowledge of the structural details of the target protein, and the target protein may even be a previously unknown protein.

In the illustrated example, the cyclic library compounds 102 are made of a polypeptide sequence of lysine (modified)-alanine (modified)-$Y^1$, $Y^2$, $Y^3$, $Y^4$, and $Y^5$-lysine (modified). The cyclic library compounds 102 are of a type of cyclic compound known as macrocyclic compounds, which refers to cyclic compounds that have twelve or more atoms or members in their ring. The amino acids $Y^1$, $Y^2$, $Y^3$, $Y^4$, and $Y^5$ are variable amino acids, in other words they can each be any amino acid, and form the variable portion 108 of the compounds in the library. Each of the lysines is modified by replacing the terminal amino group (—$NH_2$) of its sidechain with an azide group (—$N_3$). The alanine is modified by replacing one hydrogen of the methyl group (—$CH_3$) of its sidechain with an acetylene or propargyl group (—C≡CH). The acetylene or propargyl group (—C≡CH) of the modified alanine 103 reacts with the azide group (—$N_3$) of the modified lysine 105 to form a heterocyclic triazole ring 109 that bonds the sidechains of the modified lysine 105 and the modified alanine 103 together, thus forming the cyclic library compound 102. The azide group (—$N_3$) of the terminal modified lysine 111 forms the complementary clickable group 104 of the library compound 102. The portion of the cyclic library compound 102 that excludes the variable portion 108 constitutes the constant portion 106. The full or complete compound library may contain approximately 2 million or more constituent compounds, which satisfy the general formula depicted in FIG. 2.

It should be understood that the terms "modified lysine" and "modified alanine," and their equivalents are not are not intended to convey or suggest anything about the process or the precursors used to arrive at the "modified lysine" or the "modified alanine," but that these terms are used only as a way to convey the chemical structural features of these moieties in an efficient and succinct manner.

The library compounds 102 are attached to a solid support 101 by a linker 113 to form the supported library compound 100. In the illustrated Example, the linker 113 includes an ethylamine portion of the form —NH—CH$_2$—CH$_2$—. The nitrogen of the ethylamine portion is covalently bonded to the carboxyl group carbon of the modified lysine 105 and the carbon of the ethylamine portion farthest from its nitrogen is bonded to or is otherwise bound to the solid support 101. Other suitable linkers include, without limitation, polyethylene oxide chains, polypropylene oxide chains, copolymers thereof, and any combination of these with the linker 113. The solid support 101 may be selected from the group including, but not limited to, beads, multi-well ELISA plates, and BRAP chips.

In some examples herein, the target protein is reacted with a precursor that provides for the addition of clickable groups to the target protein without impacting appreciably the immunogenic determinant characteristics of the target protein. In an example herein, the precursor or reagent providing the clickable group to the target protein is propargyl-N-hydroxysuccinimidyl ester and the clickable group handle moiety 119 is an acetylene or propargyl group (—C≡CH). Such propargyl groups can bind the complementary clickable group 104 of the library compounds in a "click reaction" by forming a triazole ring in the same manner as was discussed previously in relation to the cyclization of the library compounds.

In embodiments that employ labeling, the step of labeling (120) the synthetic antigen is performed before the step of selecting (122) one or more compounds from the compound library that bind to the synthetic antigen. In some embodiments, biotin or a PEGylated biotin may be used as a detection label. In an example herein, alkaline phosphatase conjugated Rb anti-E2 pAb (retinoblastoma protein and rabbit anti-E2 polyclonal antibodies) was used as the detection label. Colorimetric-based immunoassay techniques may be used with alkaline phosphatase detection labels, whereas biotin labels are typical in all immunoassays.

In some embodiments herein, a plurality of compounds from the compound library are selected, and each compound selected binds to the synthetic antigen in such a way that the complementary click handle of the compound will simultaneously bind the click handle of the synthetic antigen. The corresponding peptide sequence for each compound selected is different from the corresponding peptide sequence for every other compound selected. In other words, each of the selected compounds is unique by virtue of its corresponding peptide sequence defined by the amino acids $Y^1$, $Y^2$, $Y^3$, $Y^4$, and $Y^5$.

In some embodiments herein, the method further comprises the step of forming (126) a construct molecule comprising one or more arms 115. The arms 115 may be formed of a polymer molecule, for instance. In general, it is believed that more arms of the construct yields improved affinity and selectivity towards the target protein. Constructs having more than one arm 115 may be referred to as "multi-arm" constructs.

Figure 3:
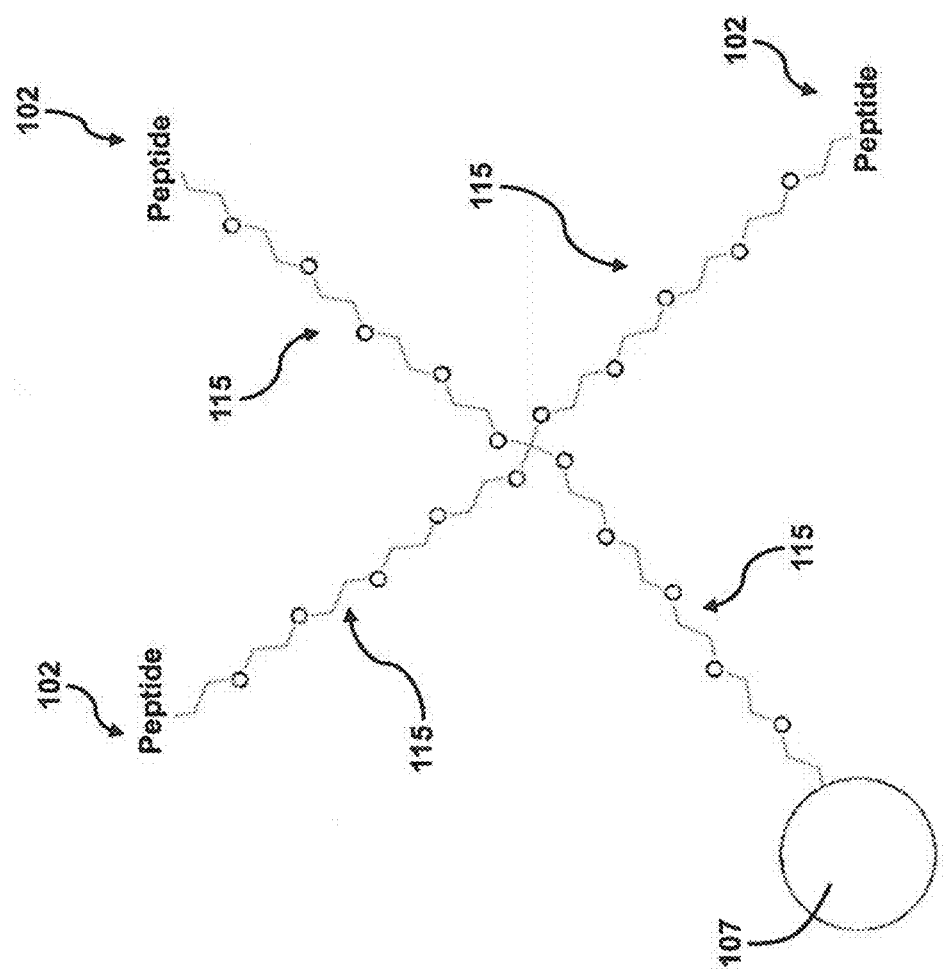
FIG. 3 illustrates schematically an embodiment of a 3-arm construct disclosed herein.

An example of a 3-arm construct can be seen in FIG. 3. Each of the plurality of arms 115 incorporates at least one cyclic polypeptide 102 chosen from among the plurality of the compounds selected based at least on their simultaneous attachment to the target protein and to one of its click handles. In the illustrated example, each arm 115 is in the form of a polyethylene oxide arm having a cyclic polypeptide 102 at one end chosen from the selected library compounds. The other end of each polyethylene oxide arm is connected to the other arms to form the multi-arm construct. In some embodiments, the multi-arm construct may further comprise an attachment 107 and at least one linker connecting the plurality of arms 115, directly or indirectly, to the attachment 107. The illustrated example of FIG. 3 shows a capture agent for a target protein. In this example, a polyethylene oxide arm 115 connects the other arms to the attachment 107, which may be a solid support of the same types as used for the solid support 101. An attachment 107 of the solid support type would not be necessary in embodiments of the construct intended as a treatment for disease. In any given embodiment of the construct, the cyclic polypeptides 102, chosen from the selected library compounds, may be the same or different from one another.

In the illustrated example of FIG. 3, the arms 115 are of the form:

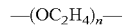

where n is greater than or equal to 1, and more preferably greater than or equal to 5.

Alternatively, in some examples, an arm 115 may have the following form:

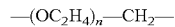

where n is greater than or equal to 1, and more preferably greater than or equal to 5.

Alternatively, in other examples, an arm 115 may have the following form:

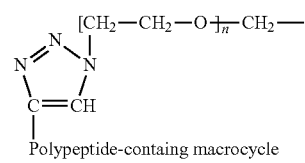

Polypeptide-containing macrocycle where n is greater than or equal to 1, and more preferably greater than or equal to 5. Arms 115 of any suitable type may be used with arms of the same type or arms of any other suitable type within the same construct.

In some embodiments, a single, 1-arm construct is selected from the group consisting of constructs having the following structure:

wherein $R^1$ is selected from the group consisting of H, OH, NH$_2$, —CONH$_2$, COOH, OC$_2$H$_5$, an attachment 107, and a linker connected to an attachment 107, and wherein $X^1$ is chosen from the library compounds selected based at least on their simultaneous attachment to the target protein and to one of its click handles; and salts, tautomers, prodrugs, and stereoisomers, including enantiomers, thereof. Accordingly, the compound $X^1$ is cyclic and includes a corresponding peptide sequence formed by a corresponding set of amino acids, such as $Y^1$, $Y^2$, $Y^3$, $Y^4$, and $Y^5$ for example. The integer n is greater than or equal to 1. In some examples, the integer n is greater than or equal to 5. In some other examples, the integer n is greater than or equal to 10.

In some embodiments, the multi-arm construct is selected from the group consisting of constructs having the following structure:

$$R^1-\underset{\underset{[OC_2H_4]_m-X^2}{|}}{\overset{\overset{[OC_2H_4]_n-X^1}{|}}{C}}-R^2$$

wherein $R^1$ is selected from the group consisting of H, OH, $NH_2$, $-CONH_2$, COOH, $OC_2H_5$, $(OC_2H_4)_k-OH$, $(OC_2H_4)_k-NH_2$, $(OC_2H_4)_k-CONH_2$, $(OC_2H_4)_k-COOH$, $(OC_2H_4)_k-OC_2H_5$, $(OC_2H_4)_k-X^4$, an attachment 107, and a linker connected to an attachment 107, wherein $R^2$ is selected from the group consisting of H, OH, $NH_2$, $-CONH_2$, COOH, $OC_2H_5$, $(OC_2H_4)_h-OH$, $(OC_2H_4)_h-NH_2$, $(OC_2H_4)_h-CONH_2$, $(OC_2H_4)_k-COOH$, $(OC_2H_4)_h-OC_2H_5$, and $(OC_2H_4)_h-X^3$, wherein n, m, k, and h are integers that are equal to or greater than one, and wherein $X^1$, $X^2$, $X^3$, and $X^4$ are chosen from the library compounds selected based at least on their simultaneous attachment to the target protein and to one of its click handles; and salts, tautomers, prodrugs, and stereoisomers, including enantiomers, thereof. Accordingly, the compounds $X^1$, $X^2$, $X^3$, and $X^4$ are cyclic and each includes a corresponding peptide sequence formed by a corresponding set of amino acids, such as $Y^1$, $Y^2$, $Y^3$, $Y^4$, and $Y^5$ for example, which may or may not be the same for any two of the compounds $X^1$, $X^2$, $X^3$, and $X^4$. In some examples, n, m, k, and h are integers greater than or equal to 5.

In some embodiments, the multi-arm construct is selected from the group consisting of constructs having the following structure:

$$R^1-\underset{\underset{[OC_2H_4]_m-X^2}{|}}{\overset{\overset{[OC_2H_4]_n-X^1}{|}}{C}}+OC_2H_4]_h-X^3$$

wherein $R^1$ is selected from the group consisting of H, OH, $NH_2$, $-CONH_2$, COOH, $OC_2H_5$, $(OC_2H_4)_k-OH$, $(OC_2H_4)_k-NH_2$, $(OC_2H_4)_k-CONH_2$, $(OC_2H_4)_k-COOH$, $(OC_2H_4)_k-OC_2H_5$, $(OC_2H_4)_k-X^4$, an attachment 107, and a linker connected to an attachment 107, wherein n, m, k, and h are integers that are equal to or greater than one, and wherein $X^1$, $X^2$, $X^3$, and $X^4$ are chosen from the library compounds selected based at least on their simultaneous attachment to the target protein and to one of its click handles; and salts, tautomers, prodrugs, and stereoisomers, including enantiomers, thereof. In some examples, n, m, k, and h are integers that are greater than or equal to 5.

In some embodiments, the multi-arm construct is selected from the group consisting of constructs having the following structure:

$$R^1-\underset{\underset{[OC_2H_4]_5-X^2}{|}}{\overset{\overset{[OC_2H_4]_5-X^1}{|}}{C}}+OC_2H_4]_5-X^3$$

wherein R1 is an attachment 107 or a linker connected to an attachment 107, and wherein $X^1$, $X^2$, and $X^3$ are chosen from the library compounds selected based at least on their simultaneous attachment to the target protein and to one of its click handles; and salts, tautomers and stereoisomers, including enantiomers, thereof. $R^1$ may be of the form $(OC_2H_4)_j-$ with the terminal carbon bonded to the attachment 107 and wherein j is equal to or greater than 1, and more preferably j is equal to or greater than 5.

In some embodiments, the multi-arm construct is selected from the group consisting of constructs having the following structure:

$$R^1-\left[\underset{\underset{[OC_2H_4]_{m_i}-X^{2(i)}}{|}}{\overset{\overset{[OC_2H_4]_{n_i}-X^{1(i)}}{|}}{C}}\right]_i-\underset{\underset{[OC_2H_4]_m-X^2}{|}}{\overset{\overset{[OC_2H_4]_n-X^1}{|}}{C}}-R^2$$

wherein $R^1$ is selected from the group consisting of H, OH, $NH_2$, $-CONH_2$, COOH, $OC_2H_5$, $(OC_2H_4)_k-OH$, $(OC_2H_4)_k-NH_2$, $(OC_2H_4)_k-CONH_2$, $(OC_2H_4)_k-COOH$, $(OC_2H_4)_k-OC_2H_5$, $(OC_2H_4)_k-X^4$, an attachment 107, and a linker connected to an attachment 107, wherein $R^2$ is selected from the group consisting of H, OH, $NH_2$, $-CONH_2$, COOH, $OC_2H_5$, $(OC_2H_4)_h-OH$, $(OC_2H_4)_h-NH_2$, $(OC_2H_4)_h-CONH_2$, $(OC_2H_4)_h-COOH$, $(OC_2H_4)_h-OC_2H_5$, and $(OC_2H_4)_h-X^3$, wherein i is an integer equal to or greater than 1, wherein n, m, $n_i$, $m_i$, k, and h are integers that are equal to or greater than one, and more preferably equal to or greater than 5, and wherein $X^1$, $X^2$, $X^{1(i)}$, $X^{2(i)}$, $X^3$, and $X^4$ are chosen from the library compounds selected based at least on their simultaneous attachment to the target protein and to one of its click handles; and salts, tautomers, prodrugs, and stereoisomers, including enantiomers, thereof.

$X^1$, $X^2$, $X^3$, and $X^4$ each comprise a variable portion consisting of the corresponding polypeptide of each of $X^1$, $X^2$, $X^3$, and $X^4$. In some embodiments, the corresponding polypeptide of each of $X^1$, $X^2$, $X^3$, and $X^4$ is selected from the group consisting of Tryptophan-Isoleucine-Tyrosine-Tyrosine-Isoleucine (SEQ ID NO: 1), Tyrosine-Tryptophan-Histidine-Tryptophan-Serine (SEQ ID NO: 2), Isoleucine-Tyrosine-Leucine-Arginine-Tyrosine (SEQ ID NO: 3), Phenylalanine-Tryptophan-Glutamine-Isoleucine-Leucine (SEQ ID NO: 4) and the D-amino acid versions of these sequences.

In some embodiments herein, the target protein is a protein from a pathogen. In some examples, the target protein is the CHIKV E2 protein.

Figure 4:
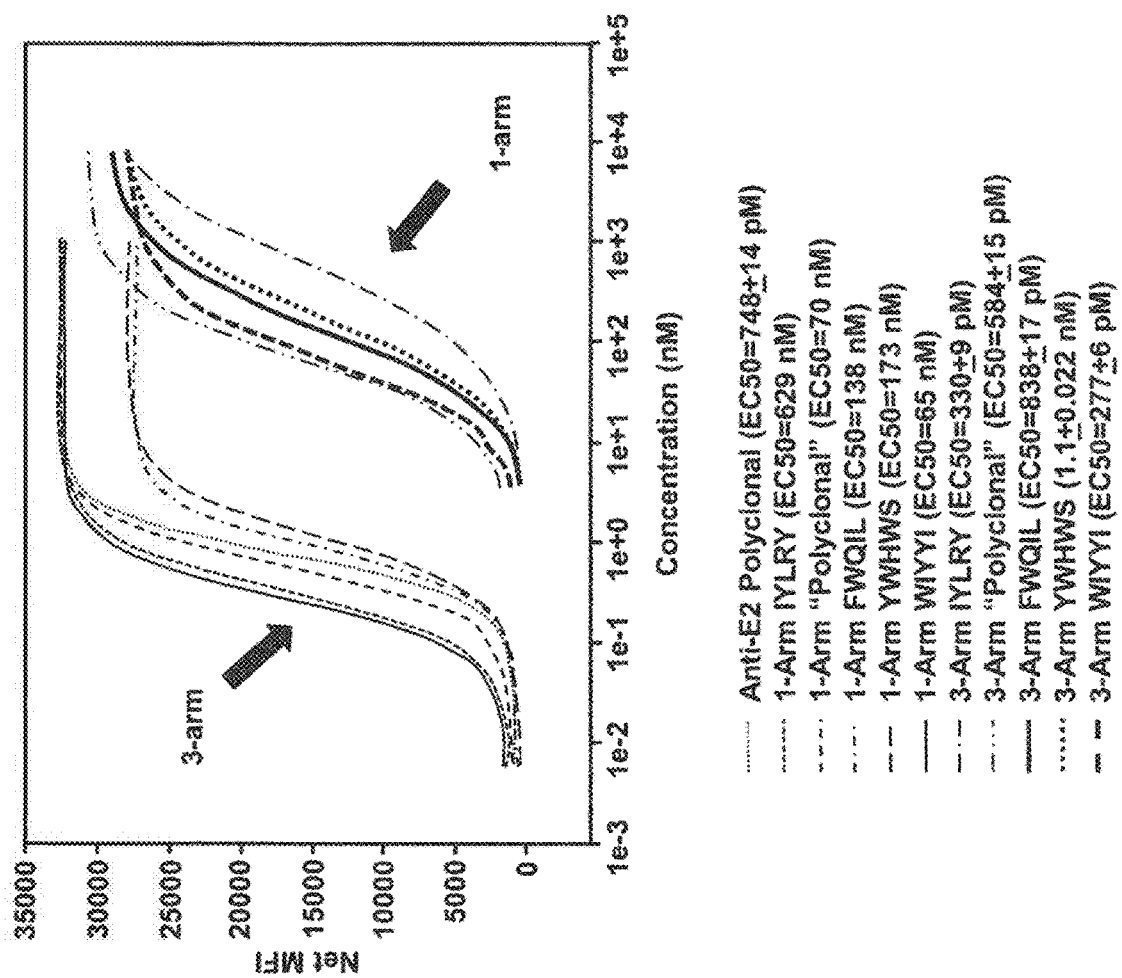
FIG. 4 is a graph illustrating the superiority of the performance of three-arm constructs disclosed herein as compared to the performance of one-arm constructs disclosed herein, the three-arm and one-arm constructs having been developed against CHIKV E2 using an embodiment of the methods disclosed herein.

Referring to FIG. 4, comparison of the performance of the disclosed three-arm constructs with one-arm constructs can be seen. The disclosed three-arm constructs show a performance improvement greater than two orders of magnitude over the one-arm constructs in terms of their affinity for the target protein by displaying the same level of binding activity as shown by achieving the same mean fluorescence intensity (MFI) at far lower concentrations of the target protein, epitope, or peptide.

Some embodiments herein are directed to pharmaceutical compositions. One embodiment herein is a pharmaceutical composition comprising a one-arm construct selected from the group consisting of constructs having the following structure:

wherein R¹ is selected from the group consisting of H, OH, NH₂, —CONH₂, COOH, OC₂H₅, an attachment 107, and a linker connected to an attachment 107, and wherein X¹ is chosen from the library compounds selected based at least on their simultaneous attachment to the target protein and to one of its click handles; and salts, PEGylation products, tautomers, prodrugs, and stereoisomers, including enantiomers, thereof. The integer n is greater than or equal to 1. In some examples, the integer n is greater than or equal to 5. In some other examples, the integer n is greater than or equal to 10. The composition also comprises a pharmaceutically acceptable carrier.

One embodiment herein is a pharmaceutical composition comprising a multi-arm construct selected from the group consisting of constructs having the following structure:

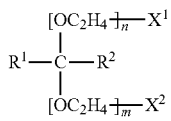

wherein R¹ is selected from the group consisting of H, OH, NH₂, —CONH₂, COOH, OC₂H₅, (OC₂H₄)$_k$—OH, (OC₂H₄)$_k$—NH₂, (OC₂H₄)$_k$—CONH₂, (OC₂H₄)$_k$—COOH, (OC₂H₄)$_k$—OC₂H₅, (OC₂H₄)$_k$—X⁴, an attachment 107, and a linker connected to an attachment 107, wherein R² is selected from the group consisting of H, OH, NH₂, —CONH₂, COOH, OC₂H₅, (OC₂H₄)$_h$—OH, (OC₂H₄)$_h$—NH₂, (OC₂H₄)$_h$—CONH₂, (OC₂H₄)$_h$—COOH, (OC₂H₄)$_h$—OC₂H₅, and (OC₂H₄)$_h$—X³, wherein n, m, k, and h are integers that are equal to or greater than one, and wherein X¹, X², X³, and X⁴ are cyclic and are chosen from the library compounds selected based at least on their simultaneous attachment to the target protein and to one of its click handles; and salts, PEGylation products, tautomers, prodrugs, and stereoisomers, including enantiomers, thereof. The composition also comprises a pharmaceutically acceptable carrier. In some embodiments, n, m, k, and h are integers that are equal to or greater than 5.

Another embodiment herein is a pharmaceutical composition comprising a multi-arm construct selected from the group consisting of constructs having the following structure:

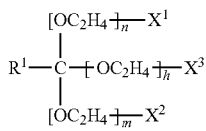

wherein R¹ is selected from the group consisting of H, OH, NH₂, —CONH₂, COOH, OC₂H₅, (OC₂H₄)$_k$—OH, (OC₂H₄)$_k$—NH₂, (OC₂H₄)$_k$—CONH₂, (OC₂H₄)$_k$—COOH, (OC₂H₄)$_k$—OC₂H₅, (OC₂H₄)$_k$—X⁴, an attachment 107, and a linker connected to an attachment 107, wherein n, m, k, and h are integers that are equal to or greater than one, and wherein X¹, X², X³, and X⁴ are cyclic and are chosen from the library compounds selected based at least on their simultaneous attachment to the target protein and to one of its click handles; and salts, tautomers, prodrugs, and stereoisomers, including enantiomers, thereof. The composition also comprises a pharmaceutically acceptable carrier. In some embodiments, n, m, k, and h are integers that are greater than or equal to 5.

Another embodiment herein is a pharmaceutical composition comprising a multi-arm construct selected from the group consisting of constructs having the following structure:

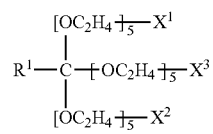

wherein R¹ is selected from the group consisting of H, OH, NH₂, —CONH₂, COOH, OC₂H₅, (OC₂H₄)$_k$—OH, (OC₂H₄)$_k$—NH₂, (OC₂H₄)$_k$—CONH₂, (OC₂H₄)$_k$—COOH, (OC₂H₄)$_k$—OC₂H₅, (OC₂H₄)$_k$—X⁴, an attachment 107, and linker connected to an attachment 107, wherein k is an integer that is equal to or greater than one, and wherein X¹, X², X³, and X⁴ each comprise a variable portion consisting of the corresponding polypeptide of each of X¹, X², X³, and X⁴, and wherein the corresponding polypeptide of each of X¹, X², X³, and X⁴ is selected from the group consisting of Tryptophan-Isoleucine-Tyrosine-Tyrosine-Isoleucine (SEQ ID NO: 1), Tyrosine-Tryptophan-Histidine-Tryptophan-Serine (SEQ ID NO: 2), Isoleucine-Tyrosine-Leucine-Arginine-Tyrosine (SEQ ID NO: 3), Phenylalanine-Tryptophan-Glutamine-Isoleucine-Leucine (SEQ ID NO: 4) and the D-amino acid versions of these sequences; and salts, tautomers and stereoisomers, including enantiomers, thereof. The composition also comprises a pharmaceutically acceptable carrier. In some examples, k is an integer that is greater than or equal to 5.

Another embodiment herein is a pharmaceutical composition comprising a multi-arm construct selected from the group consisting of constructs having the following structure:

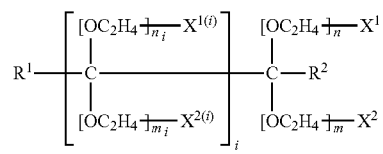

wherein R¹ is selected from the group consisting of H, OH, NH₂, —CONH₂, COOH, OC₂H₅, (OC₂H₄)$_k$—OH, (OC₂H₄)$_k$—NH₂, (OC₂H₄)$_k$—CONH₂, (OC₂H₄)$_k$—COOH, (OC₂H₄)$_k$—OC₂H₅, (OC₂H₄)$_k$—X⁴, an attachment 107, and a linker connected to an attachment 107, wherein R² is selected from the group consisting of H, OH, NH₂, —CONH₂, COOH, OC₂H₅, (OC₂H₄)$_k$—OH, (OC₂H₄)$_k$—NH₂, (OC₂H₄)$_k$—CONH₂, (OC₂H₄)$_k$—COOH, (OC₂H₄)$_k$—OC₂H₅, and (OC₂H₄)$_h$—X³, wherein i is an integer equal to or greater than 1, wherein n, m, $n_i$, $m_i$, k, and h are integers that are equal to or greater than one, and wherein X¹, X², X$^{1(i)}$, X$^{2(i)}$, X³, and X⁴ are cyclic and are chosen from the library compounds selected based at least on their simultaneous attachment to the target protein and to one of its click handles; and salts, PEGylation products, tautomers, prodrugs, and stereoisomers, including enantiomers, thereof. The composition also comprises a pharmaceutically acceptable carrier. In some examples, the integers n, m, $n_i$, $m_j$, k, and h are equal to or greater than five.

EXAMPLES

Figure 5:
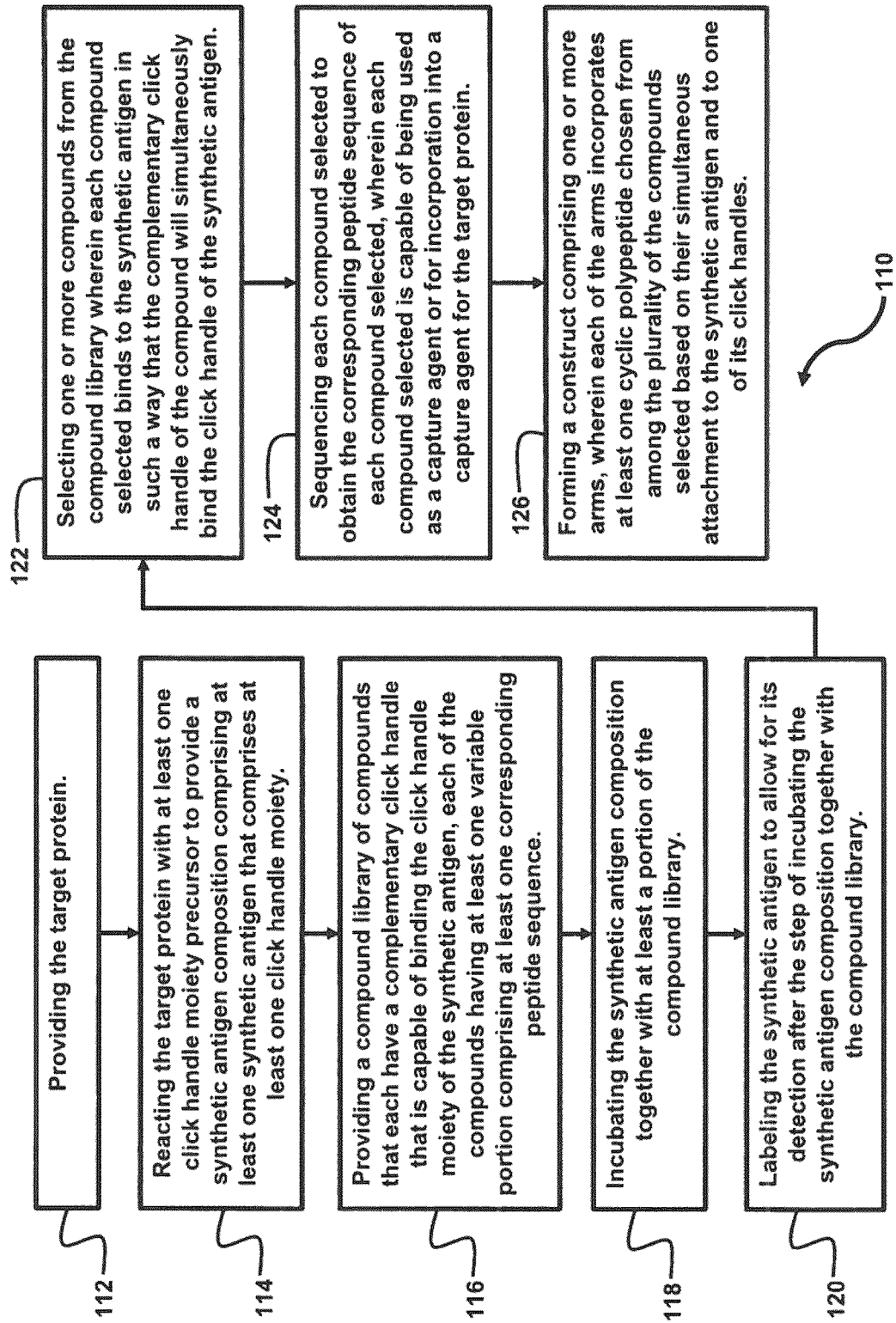
FIG. 5 is a flow diagram illustrating an embodiment of the method disclosed herein for developing a capture agent for a target protein.
Figure 6A:
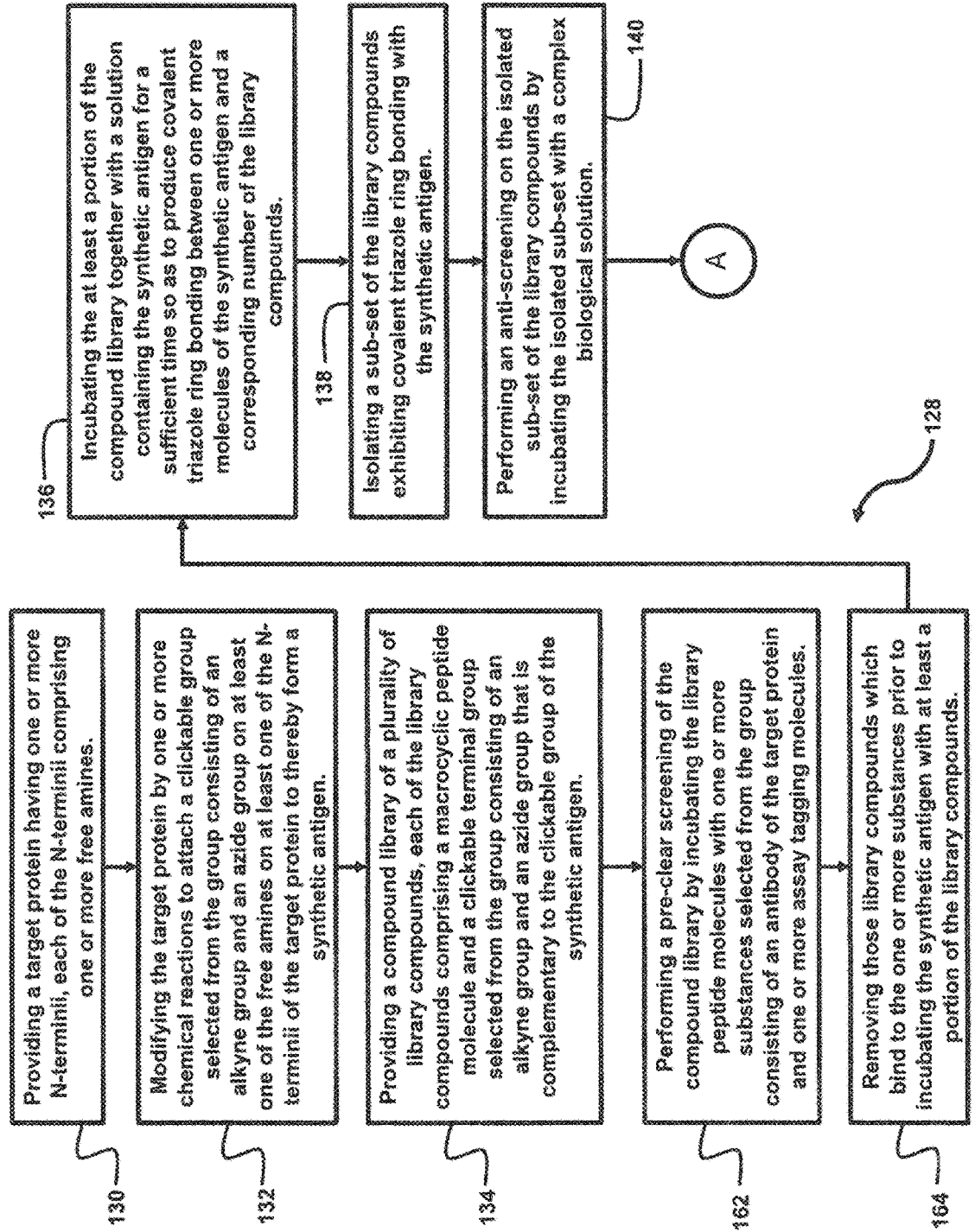
Figure 6B:
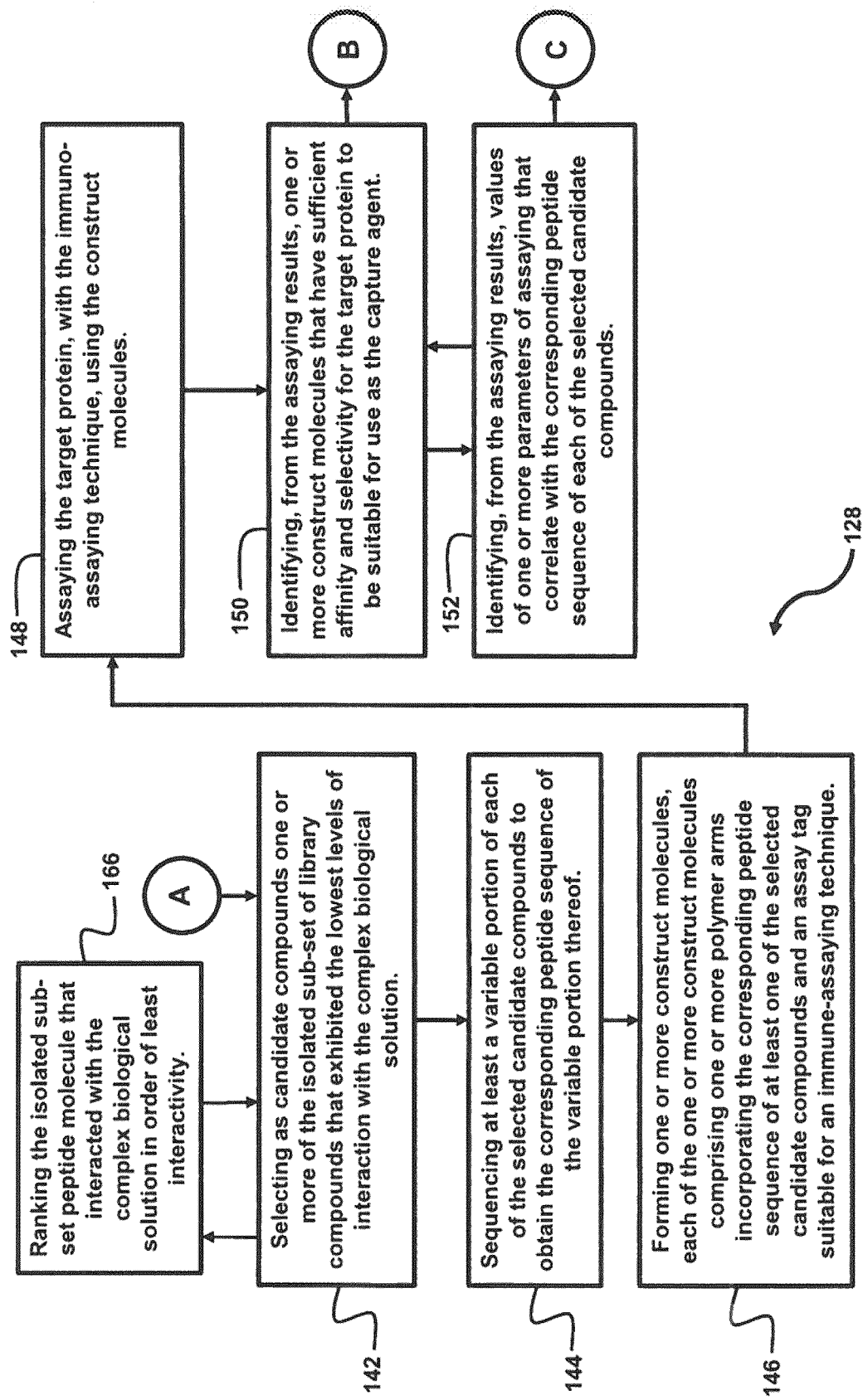

A screening strategy for the CHIKV E2 protein was performed according to the general method outlined in FIG. 5. In short, CHIKV E2 protein was functionalized with an alkyne moiety and then incubated with at least a portion of an azide terminated cyclic peptide library (architecture shown in FIGS. 1 and 2). An In situ 'click' reaction occurs between the protein and only specific cyclic peptides at the multiple substituted sites on the protein surface. The downselected cyclic peptide library members (~200 beads) were then incubated with 1% human serum to determine which members were the most selective for CHIKV E2, resulting in 4 sequences (WIYYI (SEQ ID NO: 1), YWHWS (SEQ ID NO: 2), IYLRY (SEQ ID NO: 3), FWQIL (SEQ ID NO: 4)). The detailed methodology is as follows.

Library Synthesis:

Library synthesis was achieved using similar techniques as described in the article by Das et al. (Das et al., "A General Synthetic Approach for Designing Epitope Targeted Macrocyclic Peptide Ligands," 2015, Angewandte Chemie, 54 (45), 13219-13224), which is incorporated by reference herein in its entirety.

E2 Propargylation:

CHIKV E2 antigen (1 mg/mL) was buffer exchanged into 0.5 mL of 1× phosphate buffered saline (PBS) using a 0.5 mL, 10 kDa cutoff centrifugal filter. 24.3 µL (0.243 mmol) of a 10 mM propargyl-N-hydroxysuccinimidyl ester solution in dimethyl sulfoxide (DMSO) was added to the protein solution and the reaction was incubated on ice for 2 h. The protein sample was then washed and buffer exchanged into 0.5 mL 1× PBS. Some of the protein was reacted with Biotin azide and the biotins were counted in an assay to determine average substitution of the CHIKV E2 protein by propargyl groups.

Figure 7:
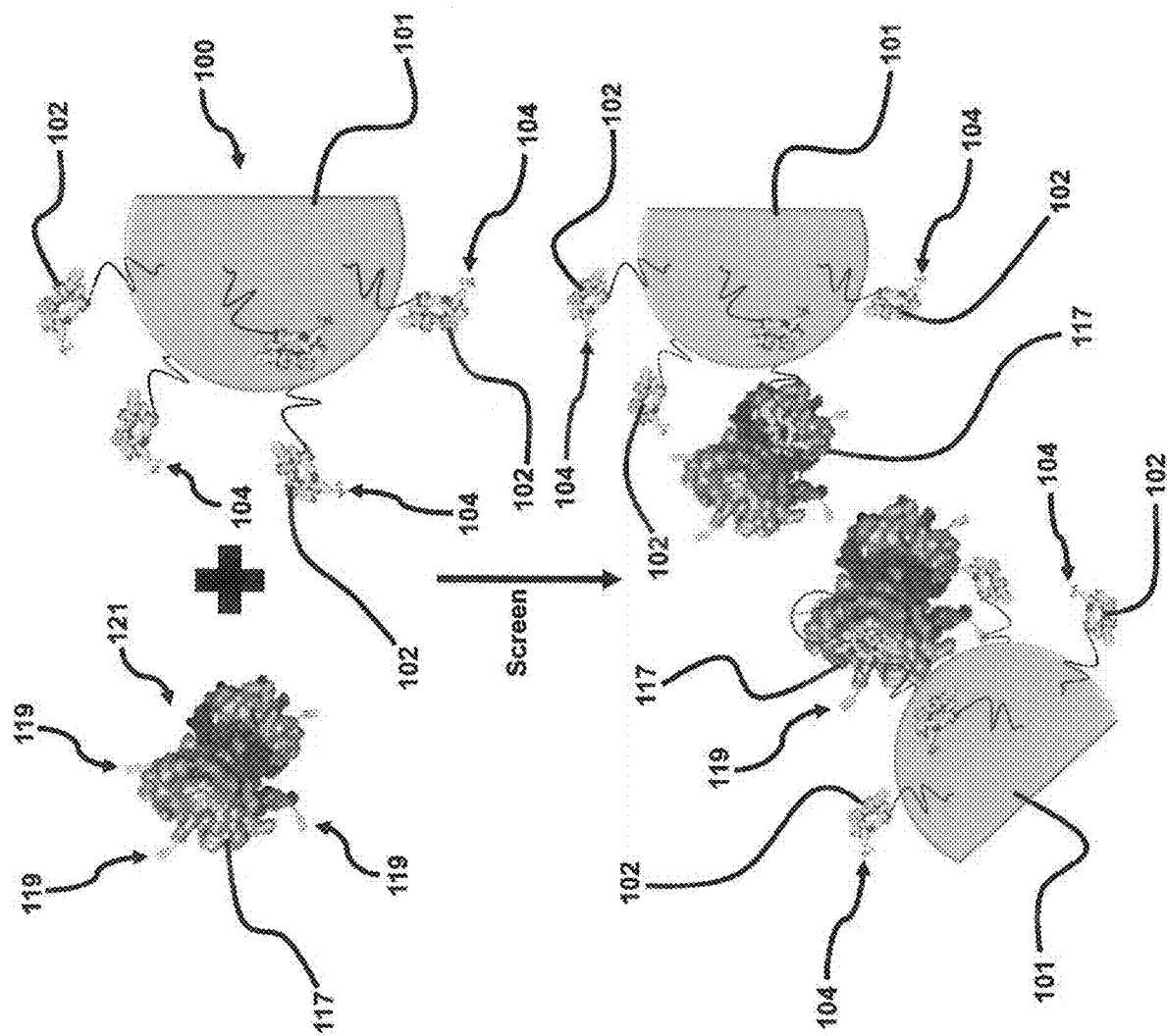
FIG. 7 is a schematic diagram illustrating a general one-bead-one-compound (OBOC) screening strategy against a propargyl-functionalized protein target in accordance with an embodiment of the methods disclosed herein, wherein circles identify triazole linkages that occur from the in situ 'click' reaction.

Screening Protocol:

The screening protocol used for developing constructs or receptors for binding to the CHIKV E2 protein is schematically mapped out in FIG. 7.

Preclear:

0.400 g of N-terminal azide cyclic library was blocked overnight at 4° C. in 10 mL of Screen Buffer (1% bovine serum albumin (BSA) in tris buffered saline (TBS)+0.1% Tween 20). The library was washed 5× with 5 mL of Screen Buffer and incubated for 1 h at 25° C. with 20 mL of streptavidin conjugated alkaline phosphatase (1:10,000 dilution), R-Phycoerythrin, biotin conjugate (1:10,000 dilution), retinoblastoma protein and rabbit anti-CHIKV E2 polyclonal antibody (Rb anti-E2 pAb) (1:10,000 dilution), and anti-Rb conjugated alkaline phosphatase (1:10,000 dilution) in Screen Buffer. The library was washed 3× with 5 mL 1% Screen Buffer, 3× with 5 mL TBS, 5× with 5 mL High Salt TBS, and 2× with 5 mL BCIP Buffer (100 mM Tris-HCl [pH 9.0], 150 mM NaCl, 1 mM $MgCl_2$). 66 µL nitro-blue tetrazolium (NBT) and 33 µL 5-Bromo-4-chloro-3-indolyl phosphate (BCIP) was added to the library suspended in 10 mL BCIP Buffer and developed for 5 min at 25° C. Development was stopped by the addition of 2 mL concentrated hydrochloric acid (HCl) and the library was washed 3× with 5 mL 1 M HCl. The library was suspended in 10 mL of 1 M HCl, and all purple beads were removed and discarded. The remaining clear resin was incubated with 10 mL of 7.5 M guanidine-HCl, pH 2.0 for 30 min and rinsed with 5 mL of deionized water 10×. The library was incubated with 10 mL N-methyl-2-pyrrolidone (NMP) for 3 h and washed with 5 mL of deionized water 10×. The term "Library" as used herein refers to the library of about 2 million compounds on solid supports in accordance with FIGS. 1 and 2, which has been previously described herein, or any subset thereof, unless otherwise specified. This treatment of the remaining clear resin, after the elimination of all purple beads, restores and conditions the corresponding library compounds in preparation for the Target Screen.

The purpose of the Preclear step is to eliminate library compounds that tend to bind compounds used for subsequent assays, such as labeling compounds and developer enzyme conjugates for example, in order to avoid a false indication that a library compound binds a target protein or a corresponding synthetic antigen.

Target Screen:

The portion of the library remaining after the preclear process, also referred to herein as the precleared library, was blocked overnight at 4° C. in 10 mL of Screen Buffer and washed 5× with 5 mL of Screen Buffer. 10 mL of 1 µM propargylated CHIKV E2 protein was added to the precleared library and incubated for 4 h at 25° C. The precleared library that has been incubated with the synthetic antigen, which is based on the target protein, may at times be referred to as the incubated, precleared library to aid in clarity. However, in the interest of simplicity, the precleared library, or the incubated, precleared library, may be simply referred to as the library when the nature of the library being referred to is clear from the context. The incubated, precleared library was washed 3× with 5 mL Screen Buffer and 10× with 5 mL TBS, followed by incubation with 7.5 M guanidine-HCl, pH 2.0 for 1 h at 25° C. After washing 6× with TBS, the incubated, precleared library was blocked for 2 h at 25° C. with 10 mL Screen Buffer. The incubated, precleared library was washed 5× with Screen Buffer and then incubated with Rb anti-E2 pAb (1:10,000 dilution) in 10 mL Screen Buffer for 1 h at 25° C. The incubated, precleared library was washed 5× with Screen Buffer and then incubated with anti-Rb conjugated alkaline phosphatase (1:10,000 dilution) in 10 mL Screen Buffer for 1 h at 25° C. After washing 3× with 5 mL of Screen Buffer, 3× with 5 mL TBS, 5× with 5 mL of High Salt TBS, and 2× with 5 mL of BCIP Buffer, the incubated, precleared library was developed as described in the Preclear. The darkest purple "hit" beads were collected, incubated with 10 mL of 7.5 M guanidine-HCl, pH 2.0 for 30 min at 25° C., and washed 10× with 5 mL deionized water. The beads were incubated with 10 mL NMP for 3 h at 25° C. and washed 10× with 5 mL deionized water. This treatment of the collected "hit" beads, after their development and collection, restores the corresponding library compounds to their original condition that they were in prior to their incubation with the synthetic antigen in preparation for the Anti-Screen.

Anti-Screen:

The "hit" bead portion of the library was blocked overnight at 4° C. in 10 mL of Screen Buffer and washed 5× with 5 mL of Screen Buffer. The "hit" bead portion of the library was then incubated with 10 mL of 1% human serum for 1 h at 25° C. After washing 3× with 5 mL of Screen Buffer, the "hit" bead portion of the library was incubated with 10 mL of Rb anti-human serum pAb (1:50,000 dilution) in Screen Buffer for 1 h at 25° C. The "hit" bead portion of the library was washed 3× with 5 mL of Screen Buffer and incubated with 10 mL of anti-Rb IgG pAb (1:10,000 dilution) in Screen Buffer for 1 h at 25° C. After washing 3× with 5 mL of Screen Buffer, 3× with 5 mL TBS, 5× with 5 mL of High Salt TBS, and 2× with 5 mL of BCIP Buffer, the "hit" bead portion of the library was developed as described in the Preclear. The beads were separated by degree of purple, where the clear beads were considered the top candidates. All separated groups of beads were incubated with 5 mL of 7.5 M guanidine-HCl, pH 2.0 for 30 min at 25° C., followed by rinsing 10× with 5 mL deionized water. The beads were then incubated with 10 mL NMP for 3 h at 25° C., washed 10× with 5 mL deionized water, and individually suspended in water overnight for sequencing. Sequencing was performed by Edman degradation.

The macrocyclic library compounds selected for incorporation into constructs or construct molecules for use as capture agents at least include the library compounds corresponding to the clear beads. The purpose of the Anti-Screen step is to eliminate library compounds that lack specificity for the target protein or the corresponding synthetic antigen and tend to generally bind proteins found in complex biological solutions such as human serum for example. Library compounds that lack this specificity would lead to false indications of the presence of the target pathogen and would bind proteins unrelated to the target pathogen, which would interfere with the normal functioning of an organism being treated for a particular infection. Accordingly, library compounds that lack sufficient specificity for the target protein are not very useful for the detection of the target pathogen or for the diagnosis and/or treatment of the related infection or disease. In the interest of simplicity, the portion of the library corresponding to the macrocyclic library compounds selected for incorporation into constructs or construct molecules for use as capture agents, or the "hit" bead portion of the library, may be simply referred to as the library when the nature of the portion of the library being referred to is clear from the context.

The developed cyclic peptides were then matured into three-arm constructs, as described in FIG. 3, which improved E2 binding by over 2 orders of magnitude (FIG. 4) and greatly improved selectivity for CHIKV E2 out of various concentrations of human serum compared to the one-arm constructs. Two of the multi-arm constructs are comparable in performance to a commercially available antibody raised against E2, while three others outperform the antibody, especially the WIYYI (SEQ ID NO: 1) multi-arm construct. The "maturation" process entails attaching the developed peptides to the one-arm or multi-arm constructs. In the illustrated example, the developed peptides are attached to three-arm constructs as shown in FIG. 3. The binding performance of the peptides is significantly improved through their incorporation into a multi-arm construct. Again, in general, it is believed that more arms of the construct yields improved affinity and selectivity towards the target protein.

Referring to FIG. 4, the binding performance of each capture agent is determined using a LUMINEX® binding assay, which is essentially the same as a sandwich-type ELISA, where the peptides are attached to a bead as a one-arm polyethylene glycol (PEG) or three-arm PEG construct. By allowing these beads to interact with varying concentrations of the CHIKV E2 protein, one can determine and compare the binding performance of each capture agent construct. A smaller value of the variable on the horizontal axis at the inflection point of a given plot for a corresponding capture agent indicates stronger binding for the corresponding capture agent with respect to the target protein or target molecule.

Experimental details of the assay techniques used herein and of the peptide synthesis techniques used herein can be found in Coppock et al., "Protein catalyzed Capture Agents with Tailored Performance for in Vitro and In Vivo Applications," 2017, Peptide Science, 108 (2), e22934, and its Supplementary Data (Appendix A), which are incorporated by reference herein in their entirety.

The screening methodology enables the development of cyclic peptide capture agents for sensing, diagnostics, and therapeutics against protein targets without the need of any structural information of the protein itself. As new biological threats and pathogens emerge, it is ideal to create reagents and receptors against these threats to help with rapid treatment and detection as full characterization occurs. While the described method was used for CHIKV E2, it can easily be repeated for any protein target. Alphaviruses, such as CHIKV, are recognized as a significant threat to both national security and public health. Although natural infection in the United States is relatively low, Alphaviruses have been the subject of significant interest in historical biological weapon development programs due to their high infectivity when aerosolized, ease of large scale production, stability under a wide range of environmental conditions, and proven tractability to genetic manipulation. Despite their importance, no licensed antivirals or vaccines are currently available to the general population in the USA. The developed reagents are capable of early detection of CHIKV and could potentially be used as therapeutics to prevent or treat CHIKV infection.

In general, these cyclic peptides used by some embodiments herein exhibit high thermal stabilities, translating to an elimination of a shipment cold chain and refrigeration for storage. Both L-amino acids and D-amino acids are contemplated for use in the cyclic peptides of the embodiments herein. The illustrated examples employ L-amino acids for both the variable and the constant portions of the cyclic peptides. The cyclic peptides may be made more biologically stable when they are composed of non-natural amino acids, such as D amino acids. Also, using on-demand synthesis and scale-up capabilities through robotic methods results in reduced batch-to-batch variation in performance.

The screening methodology employed in some embodiments herein is specifically designed to not require any structural information of the protein target, unlike many common screening techniques, allowing rapid receptor development against emerging and poorly characterized protein targets, such as biological threats and medically relevant proteins. The developed constructs are designed to bind the immunogenic, E2 surface protein of CHIKV, which could have therapeutic uses and early detection implications. There is currently no commercial vaccine available for CHIKV and since E2 protein binding to human cells is crucial to CHIKV infection, these reagents have the potential to outcompete E2/human interactions, thus preventing infection. Additionally, the gold standard for CHIKV infection detection actually requires a person to already be infected with the virus, so having a receptor that is capable of detecting the virus pre-infection is very advantageous.

Referring to FIGS. 6A-6D, some embodiments herein are directed to a method 128 for developing a capture agent for identification of a target protein. The method includes the steps of providing (130) a target protein having at least one N-terminus comprising one free amine, and/or at least one lysine amino acid, and modifying (132) the target protein by one or more chemical reactions to attach a clickable group selected from the group consisting of an alkyne group and an azide group on the free amine of the at least one N-terminus of the target protein and/or on the at least one lysine amino acid to thereby form a synthetic antigen. By definition, the N-terminus of a protein or peptide refers to the free amine (—$NH_2$) of an amino acid at an end of the peptide or polypeptide chain. The method 128 includes the further steps of providing (134) a compound library of a plurality of library compounds, each of the library compounds comprising a macrocyclic peptide molecule and a clickable terminal group selected from the group consisting of an alkyne group and an azide group that is complementary to the clickable group of the synthetic antigen; and incubating (136) the at least a portion of the compound library together with a solution containing the synthetic antigen for a sufficient time so as to produce covalent triazole ring bonding between one or more molecules of the synthetic antigen and a corresponding number of the library compounds.

After the incubation step, a target-screen assay, for example, is performed to identify and separate out library compounds that bind the synthetic antigen. Accordingly, the method includes the additional step of isolating (138) a sub-set of the library compounds exhibiting covalent triazole ring bonding with the synthetic antigen. The isolated sub-set of the library compounds are then treated to restore them to a condition where they are not occupied by any bound synthetic antigen, which may also include removal of any unreacted click moieties, in preparation for performing an anti-screen.

The method 128 additionally includes the step of performing (140) an anti-screening on the isolated sub-set of the library compounds by incubating the isolated sub-set with a complex biological solution. Examples of complex biological solutions include, but are not limited to, human or animal serum and blood. The purpose of the anti-screening step is to eliminate library compounds that lack specificity for the target protein as previously explained.

As part of the anti-screening, the method 128 includes the additional step of selecting (142) as candidate compounds one or more of the isolated sub-set of library compounds that exhibited the lowest levels of interaction with the complex biological solution. Ideally, some of the isolated sub-set of library compounds will exhibit no binding or interaction with non-target proteins in the complex biological solution and these would be considered to be the most likely candidates to be best suited for use in capture agents for the target protein. However, some of the isolated sub-set of library compounds that exhibit comparatively low levels of interaction with non-target proteins, or that exhibit the several or the few lowest levels of interaction, may also be considered as candidates for use in capture agents for the target protein.

Figure 8B:
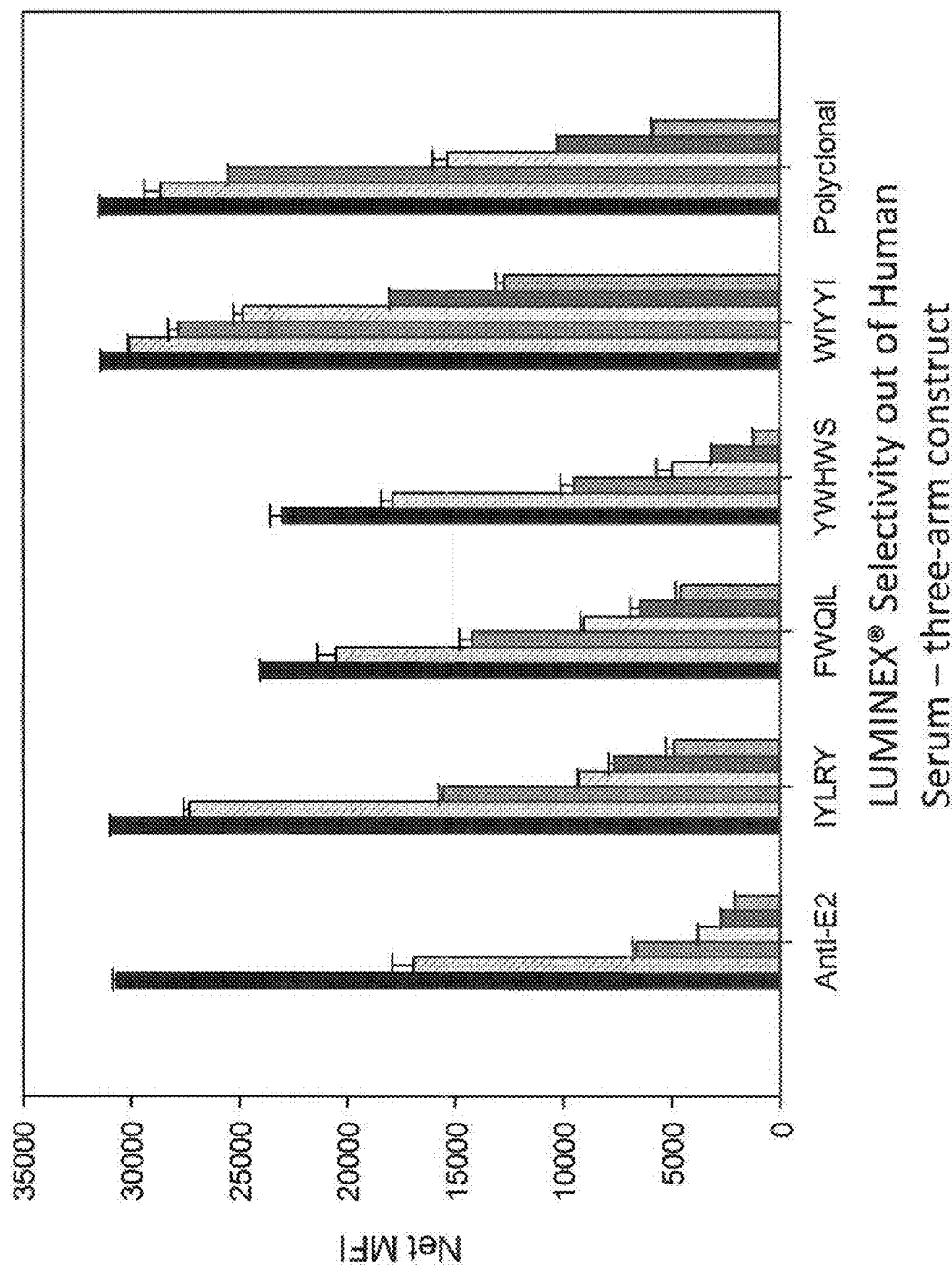

The method 128 includes the additional step of sequencing (144) at least a variable portion of each of the selected candidate compounds to obtain the corresponding peptide sequence of the variable portion thereof. Sequencing the candidate compounds is followed by the step of forming (146) one or more construct molecules, which are also referred to herein simply as constructs. Each of the one or more construct molecules comprises one or more polymer arms incorporating the corresponding peptide sequence of at least one of the selected candidate compounds and an assay tag suitable for an immune-assaying technique. The assaying results produced by the immune-assaying technique allows the identification of those construct molecules that exhibit the required affinity and selectivity, or specificity, for the target protein that would allow the identified construct molecules to serve as a capture agent for the target protein. Accordingly, the method 128 includes the additional steps of assaying (148) the target protein, with the immuno-assaying technique, using the construct molecules; and identifying (150), from the assaying results, one or more construct molecules that have sufficient affinity (see FIG. 4) and selectivity (see FIGS. 8A-8B) for the target protein to be suitable for use as the capture agent. Identifying the construct molecules that have sufficient affinity and selectivity for the target protein to be suitable for use as capture agents involves the step of identifying (152), from the assaying results, values of one or more parameters of assaying that correlate with the corresponding peptide sequence of each of the selected candidate compounds. An example of such parameters of assaying that correlate with the peptide sequences of the candidate compounds is the Net Median Fluorescent Intensity (Net MFI) of FIG. 4, the values of which for each corresponding candidate compound and peptide sequence are indicative of the affinity, as shown in FIG. 4, and selectivity, as shown in FIGS. 8A-8B, when applied to solutions with varying concentrations of non-target proteins, of the candidate compounds for the target protein. The particular parameter of assaying would, of course, vary depending upon the type of assay being used.

The capture agents developed using the embodiments herein can be used in methods for identification of the presence of the target protein in a sample, such as a biological sample for example. An embodiment of such an identification method may comprise obtaining (154) a sample to screen for the target protein; assaying (156) the sample using the capture agent developed using the methods herein and using the same immuno-assaying technique used in identifying the construct molecule that is used as the capture agent; and identifying (158) whether the sample comprises the target protein from the values for the one or more parameters of assaying obtained from the assaying results.

The peptide constructs can be used to identify, detect, quantify, and/or separate the protein target in a biological sample. In certain embodiments, these methods utilize an immunoassay, with the capture agent replacing an antibody or its equivalent. In certain embodiments, the immunoassay may be, but not limited to, a Western blot, pull-down assay, dot blot, ELISA, or other immunoassays described in Vashist, S. K. and Luong, J. H. T. Handbook of Immunoassay Techniques 2018, which is incorporated by reference herein in its entirety. Various immunoassay techniques are summarized in the table of contents of that handbook which can be used.

A biological sample for use in the methods provided herein may be selected from the group consisting of organs, tissue, bodily fluids, and cells. Where the biological sample is a bodily fluid, the fluid may be selected from the group consisting of blood, serum, plasma, urine, sputum, saliva, stool, spinal fluid, cerebral spinal fluid, lymph fluid, skin secretions, respiratory secretions, intestinal secretions, genitourinary tract secretions, tears, and milk. The organs include, e.g., the adrenal glands, bladder, bones, brain, breasts, cervix, esophagus, eyes, gall bladder, genitals, heart, kidneys, large intestine, liver, lungs, lymph nodes, ovaries, pancreas, pituitary gland, prostate, salivary glands, skeletal muscles, skin, small intestine, spinal cord, spleen, stomach, thymus gland, trachea, thyroid, testes, ureters, and urethra. Tissues include, e.g., epithelial, connective, nervous, and muscle tissues. Other samples could also include, but not limited to, water, food, and other environmental samples.

Provided herein in certain embodiments are methods of using the peptide constructs disclosed herein to detect and/or diagnose the antigen. In certain of these embodiments, the methods comprise (a) obtaining a biological sample from a subject and/or environment; (b) measuring the presence or absence of antigen in the sample with a peptide construct; and (c) comparing the levels of antigen to a predetermined control range for antigen.

One embodiment herein relates to a method for inhibiting infection of a host by a pathogen associated with the target protein using the corresponding peptide sequence of at least one of the selected candidate compounds developed using the methods herein. The inhibiting method comprises administering (160) a pharmaceutical formulation comprising a pharmaceutically acceptable construct molecule comprising one or more polymer arms incorporating the corresponding peptide sequence of at least one of the selected candidate compounds identical to that used in the construct molecule found suitable for use as a capture agent in accordance with the methods herein to the host. The corresponding peptide sequence interacts with the target protein in the host to bind to the pathogen and impede the pathogen's ability to carry out its pathogenic actions or functions. In one of the examples herein, the target protein comprises the Chikungunya virus (CHIKV) E2 surface protein. The capture agent or construct molecule for in vivo use would have to be pharmaceutically acceptable and could not incorporate an assay tag whose toxicity would outweigh the therapeutic benefits of the construct molecule. Furthermore, the capture agent or construct molecule for in vivo use would likely not incorporate an assay tag at all if less toxic replacement substituents are available for any given assay tag.

In other embodiments, the peptide constructs disclosed within can used as a specific targeted in vivo and/or in vitro inhibitor and/or therapeutic. In certain aspects of this embodiment, a peptide construct is administered alone without delivering DNA, a radiopharmaceutical or another active agent.

Therapeutic agents and the peptide constructs disclosed herein can be linked or fused in known ways, optionally using the same type of linkers discussed elsewhere in this application. Preferred linkers will be substituted or unsubstituted alkyl chains, amino acid chains, polyethylene glycol chains, and other simple polymeric linkers known in the art. More preferably, if the therapeutic agent is itself a protein, for which the encoding DNA sequence is known, the therapeutic protein and antigen binding polypeptide can be coexpressed from the same synthetic gene, created using recombinant DNA techniques, as described above. The coding sequence for the antigen binding peptide construct can be fused in frame with that of the therapeutic protein, such that the peptide is expressed at the amino- or carboxy-terminus of the therapeutic protein, or at a place between the termini, if it is determined that such placement would not destroy the required biological function of either the therapeutic protein or the antigen binding peptide construct. A particular advantage of this general approach is that concatamerization of multiple, tandemly arranged peptide constructs is possible, thereby increasing the number and concentration of antigen binding sites associated with each therapeutic protein. In this manner, antigen binding avidity is increased, which would be expected to improve the efficacy of the recombinant therapeutic fusion protein.

In some embodiments herein, the corresponding peptide sequence of the selected candidate compounds is selected from the group consisting of Tryptophan-Isoleucine-Tyrosine-Tyrosine-Isoleucine (SEQ ID NO: 1), Tyrosine-Tryptophan-Histidine-Tryptophan-Serine (SEQ ID NO: 2), Isoleucine-Tyrosine-Leucine-Arginine-Tyrosine (SEQ ID NO: 3), Phenylalanine-Tryptophan-Glutamine-Isoleucine-Leucine (SEQ ID NO: 4) and the D-amino acid versions of these sequences.

In some embodiments herein, the method for developing a capture agent further comprises performing (162) a pre-clear screening of the compound library by incubating the library peptide molecules with one or more substances selected from the group consisting of an antibody of the target protein and one or more assay tagging molecules and subsequently removing (164) those library compounds which bind to the one or more substances prior to incubating the synthetic antigen with at least a portion of the library compounds. As previously stated, the pre-clear step or screening has the benefit of eliminating library compounds that tend to bind compounds used for subsequent assays, which would lead to a false indication that a library compound binds to a target protein.

In some embodiments herein, the anti-screening step further comprises ranking (166) the isolated sub-set peptide molecule that interacted with the complex biological solution in order of least interactivity.

In certain embodiments, the attachment 107 may comprise, but is not limited to, H, OH, $NH_2$, COOH, $OC_2H_5$, —$C(O)NH_2$, an amino acid, polymer-based beads, dyed polymer-based beads, fluorescent beads, quantum dots, nanoparticles, magnetic beads, any of the solid supports enumerated for solid support 101, or various surfaces such as, but not limited to, gold or other metals, silicon, graphene, or polymeric surfaces.

In certain embodiments, the attachment 107 may comprise a detection label, including for example biotin, horseradish peroxidase, alkaline phosphatase, luminol, isoluminol and their derivatives, acridinium ester derivative, copper-1, 4,7,10-tetraazacyclododecane-1,4,7,10-tetraacetic acid (copper-DOTA), $^{64}$Cu DOTA, $^{68}$Ga DOTA, $^{18F}$, $^{64}$Cu, 68Ga, 89Zr, $^{124}$I, $^{86}$Y, $^{94m}$Tc, $^{110m}$In, 11C, $^{76}$Br, $^{123}$I, $^{131}$I, $^{67}$Ga, $^{111}$In and $^{99m}$Tc, or other radiolabeled products that may include gamma emitters, proton emitters, positron emitters, tritium, or covered tags detectable by other methods (i.e., gadolinium) among others.

In certain embodiments, the attachment 107 may comprise a fluorophore including, but not limited to, Alexa Fluor, Pacific Blue, coumarin, BODIPY, Pacific Green, Oregon Green, Fluorescein, Cy3, Pacific Orange, Tetramethylrhodamine, Texas Red, Cy5, eFluor, Super Bright, R-Phycoerythrin, or Allophycocyanin. In addition, the solid support 101 of the library compounds may be replaced by any of the tags, labels, or supports enumerated for the attachment 107.

Certain tagged embodiments of the construct molecules herein are used as capture and/or detection agents in a variety of immunoassays, such as, but not limited to, enzyme-linked immunoassays, surface plasmon resonance-based immunoassays, lateral flow immunoassays, electrochemical-based immunoassays, paper-based immunoassays, fluorescence-based immunoassays, DNA-based immunoassays, radioactive-based immunoassays, label-free immunoassays, chemiluminescence-based immunoassays, acoustic wave-based immunoassays, interferometry-based immunoassays, nanomaterial- and micromaterial-based immunoassays, microcantilever-based immunoassays, optical-based immunoassays, magnetic-based immunoassays, microarray immunoassays, quartz crystal microbalance-based immunoassays, Lab-on-a-Chip (LOC) immunoassays, smartphone-based immunoassays, and wearable immunoassays.

The pharmaceutical compositions of the embodiments herein may be administered to any part, organ, interstice or cavity of a human or non-human body that is subject to an infection. For example, the composition may be administered by, but not limited to, oral and non-oral preparations (e.g., intramuscular, subcutaneous, transdermal, visceral, IV (intravenous), IP (intraperitoneal), intraarticular, placement in the ear, ICV (intracerebralventricular), intraarterial, intrathecal, intracapsular, intraorbital, injectable, pulmonary, nasal, rectal, and uterine-transmucosal preparations).

Carriers may be selected by one skilled in the art. Examples of pharmaceutically acceptable carriers, which are suitable for use in the formulations of the embodiments herein, include, without limitation, any and all solvents, diluents, or other vehicle, dispersion or suspension aids, surface active agents, isotonic agents, thickening or emulsifying agents, preservatives, stabilizers, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the embodiments herein, such as by producing any undesirable biological effect or otherwise interacting in a deleterious manner with any other component(s) of the pharmaceutical composition, its use is contemplated to be within the scope of the embodiments herein. Some examples of materials which can also serve as pharmaceutically acceptable carriers include, but are not limited to, sterile water or saline, glycerin, or mixtures thereof, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; dimethyl sulfoxide (DMSO); excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; calcium phosphate; dextran; pectin; dextrin; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition. Additionally, the carrier or diluent may include a time delay material, such as glycerol monostearate or glycerol distearate alone or with a wax. In addition, slow release polymer formulations may be used.

The pharmaceutical compositions herein are preferably formulated in dosage unit form for ease of administration and uniformity of dosage. The expression "dosage unit form" as used herein refers to a physically discrete unit of treating agent appropriate for the patient to be treated. As is normally the case, the total daily usage of the treating agents, their derivatives, and formulations of the embodiments herein will be decided by the attending physician using routine reliance upon sound medical judgment. The specific therapeutically effective dose level for any particular patient or organism will depend upon a variety of factors including the disorder being treated; the severity of the disorder; the severity of side effects; the potency of the specific agent or derivative employed; the specific composition employed; the age, body weight, general health, sex and diet of the patient; the route and schedule of administration; the rate of metabolism and/or excretion of the treating agent or its derivatives or metabolic products; the duration of the treatment; drugs used in combination or coincident with administration of the agent or derivative of the embodiments herein; and like factors well known in the medical arts.

Referring to FIG. 4, the assay for an illustrative example was performed on a LUMINEX® 200 instrument. LUMINEX®'s xMAP technology drives multiplexed assay capabilities by combining fluidics, optics, and digital signal processing with microsphere technology. The LUMINEX® 200 is capable of testing up to 100 analytes simultaneously from a single sample and is the leading multiplex immunoassay technology. In general, the color-coded microspheres are the substrate on which the solution phase assays are performed, where a specific microsphere color corresponds to an individual receptor attached to the microsphere surface.

In one illustrative example, 6 separate microsphere regions were first functionalized with a single arm polyethlyglycine (PEG) azide molecule. Each microsphere region was then reacted with an individual, alkyne-functionalized cyclic peptide (with the sequence WIYYI, IYLRY, YWHWS, FWQIL), or an equal combination of all sequences (noted as "polyclonal"). As a control, polyclonal Anti-E2 antibody was attached to a bead region for performance comparison against the peptide constructs. In an analogous experiment, the exact same process was repeated, except the single arm PEG azide molecule was switched to a 3-arm PEG azide molecule.

The details of some of the synthesis and experimental techniques useful in the embodiments herein can be found in United States Patent Application Publication No. US 2017/0349754 A1, by Matthew B. Coppock, published Dec. 7, 2017, M. B. Coppock et al., "A novel discovery, maturation, and assay integration approach for the development of ruggedized multi-valent capture receptors exemplified against the chikungunya virus E2 protein," Sensing and Bio-Sensing Research 22 (2019) 100248, and M. B. Coppock, D. N. Stratis-Cullum, "A universal method for the functionalization of dyed magnetic microspheres with peptides," Methods 158 (2019) 12-16, all of which, including their supplemental parts and appendices, are incorporated by reference herein in their entirety. The 6 separate microsphere regions (one experiment was performed with all the single-arms and another experiment was performed with all the 3-arms) may be formed, for example, using the specific chemistry illustrated in Scheme 1 of the Methods (2019) article. Once formed, they were combined in 24 wells of a 96-well plate. In duplicate, each well was incubated with varying concentrations of biotin conjugated CHIKV E2 protein (12 solutions total). The biotin conjugated on the protein is a common method of preparing the protein for detection in these early studies. Streptavidin phycoerythrin conjugate was then added to each of the 24 wells which fluorescently labels all of the protein that is attached to the microsphere through interaction with the peptide receptors on the surface. This is considered a sandwich-type assay because the protein is bound to the microsphere via the peptides and the detection conjugate (streptavidin phycoerythrin) is attached the protein via the biotin-streptavidin interaction.

Each solution in the well is then injected into the LUMINEX® instrument and the identity, or region, of the microsphere is determined by a laser (so it identifies which peptide is on the microsphere) and the amount of protein attached to the microsphere is determined by another laser that measures the fluorescence intensity of the phycoerythrin bound to the protein (this is shown as MFI, or Median Fluorescent Intensity, on the y-axis of the data). The best performing peptides will be able to show the highest MFI at the lowest concentrations of E2 protein added. The EC50 (Half Maximal Concentration) calculation is a typical way to compare binding performance and is just the inflection point of each plot. The lower the EC50, the stronger the binder.

Based on this experiment, it is clear that a trend is appearing where more arms correspond to stronger binding, or lower EC50 values. The experiments were only performed with 1-arm and 3-arm, but the molecules are not limited to these and could be 2-arm, 4-arm, etc.

Referring to FIGS. 8A-8B, data has also been gathered by the present inventor that shows the selectivity of each peptide (1-arm and 3-arm) for biotin CHIKV E2 from various concentrations of human serum. Human serum was chosen due to the high amount of random biological molecules within the solution. The maturation of the macrocycles to multi-valent forms, through functionalization of a multi-arm PEG, resulted in an over 200-fold affinity improvement and significant capture abilities in 0-50% (v/v) human serum, compared to other designed peptide reagents against other protein targets, versus the individual mono-ligand components. In fact, there is a general increase in the MFI magnitude ratios of multi to mono ligands as the human serum concentration is increased, suggesting that the multi-valent embodiments are truly capable of better binding performance in the presence of increasing human serum concentrations.

Figure 9:
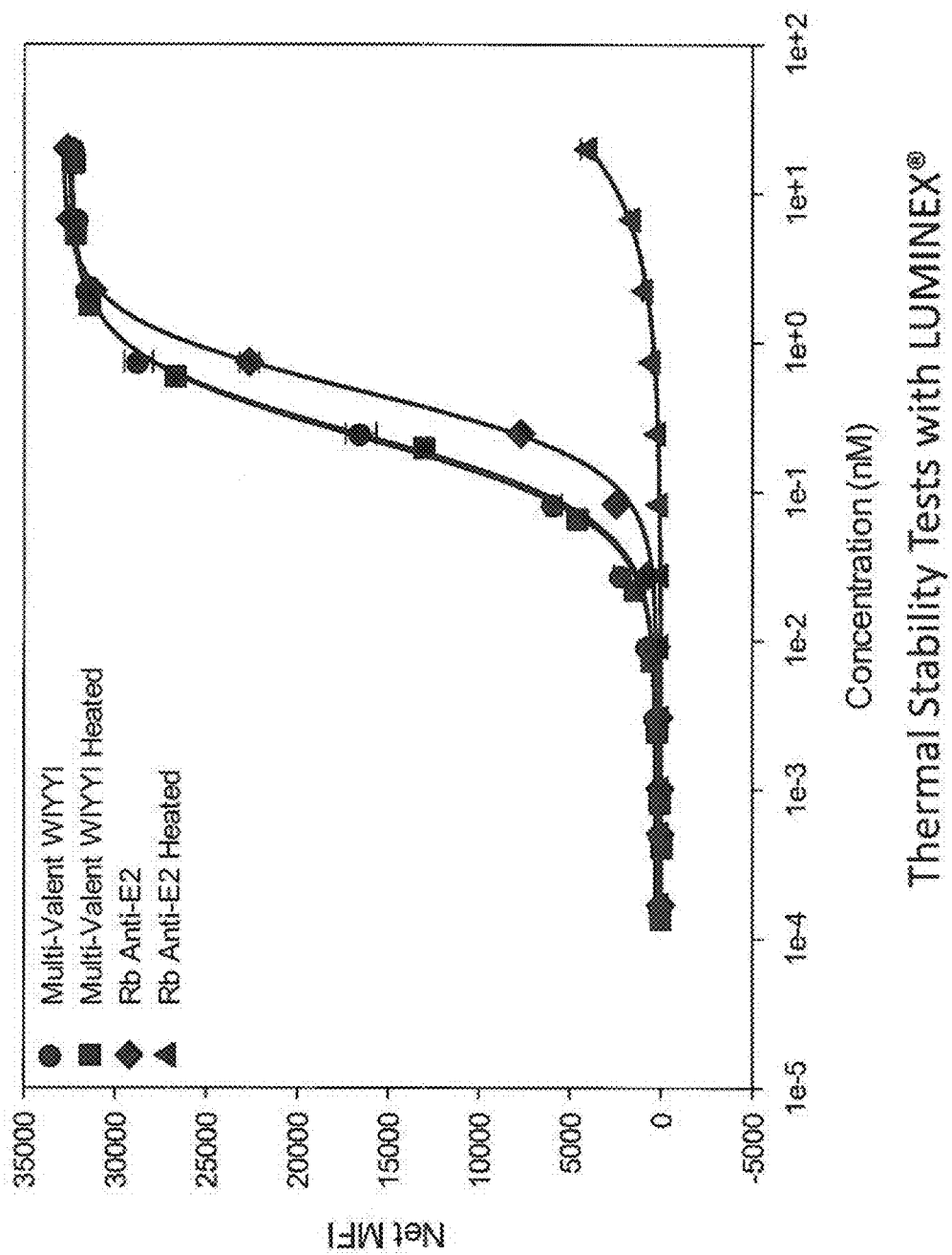
FIG. 9 is a graph illustrating the results of a LUMINEX® assay comparison of the binding affinity of a 3-arm WIYYI-containing construct and Rabbit anti-E2 antibody for CHIKV E2 before and after heating at 90° C. for 1 hour.

The best performing macrocycle comprising peptide sequence WIYYI (SEQ ID NO: 1) was heated to determine the thermal stability, and more importantly, the remaining binding activity in comparison to the Rabbit anti-E2 antibody. For this experiment, solubilized alkyne terminated WIYYI-containing macrocycle (the structure described in FIG. 2, but without the bead 101, the C terminus is an amide) and Rabbit anti-E2 antibody were heated at 90° C. for 1 hr. or left unheated as a control. After heating, the WIYYI-containing macrocycle was then added to the bead functionalized with the 3-arm linker to form the 3-arm construct of the WIYYI-containing macrocycle. The data in FIG. 9 compares the binding activity of both the 3-arm construct of the WIYYI-containing macrocycle and Rabbit anti-E2 before heating (WIYYI EC50=0.232±0.006 nM; Rb anti-E2 EC50=0.478±0.007 nM) and subsequent binding activity after heating (WIYYI EC50=0.245±0.005 nM; Rb anti-E2 EC50=N/A). The 3-arm WIYYI-containing construct shows no loss in binding activity after heating, whereas the Rb anti-E2 antibody loses its binding activity.

In general, these peptides will work in any assay considered an immunoassay. They can be used in both label (as the receptor or labeled as the detection) and label-free (as the receptor) iterations of such immunoassays. Some examples are Luminex (as shown), Enzyme Linked Immunosorbent Assay (ELISA), Surface Plasmon Resonance (SPR), etc.

Besides detection assays, these molecules could be used in therapeutic or inhibitor applications. The CHIKV E2 protein is a surface protein that creates an immune response with the host and is involved in the first step of virus infection. The pre-attaching of the E2 protein to one of these peptides could potentially reduce or prevent infection from occurring. It could also out-compete other binding molecules to reduce the spread of the infection in the host.

Peptides and polypeptides are used interchangeably herein. The amino acids referred to herein are all L-form amino acids except for glycine, which does not form enantiomers, except as otherwise specifically noted. "Salts" as used herein means "pharmaceutically acceptable salts." "Pharmaceutically acceptable salt" includes both acid and base addition salts.

The foregoing description of the specific embodiments will so fully reveal the general nature of the embodiments herein that others may, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein may be practiced with modification within the spirit and scope of the appended claims.

What is claimed is:

1. A method for developing a capture agent for a target protein, the method comprising:
   providing a whole protein as the target protein;
   modifying the whole target protein so as to make it capable of binding with at least one click handle moiety precursor without having prior knowledge of the structure of the whole target protein;
   reacting the modified whole target protein with the at least one click handle moiety precursor to provide a synthetic antigen composition comprising at least one synthetic antigen that comprises the modified whole target protein and at least one click handle moiety;
   providing a compound library of compounds that each have a complementary click handle that is capable of binding the click handle moiety of the synthetic antigen, each of the compounds having at least one variable portion comprising at least one corresponding peptide sequence;
   incubating the synthetic antigen composition together with at least a portion of the compound library;
   selecting one or more compounds from the compound library such that each compound selected binds to the synthetic antigen in such a way that the complementary click handle of the compound will simultaneously bind the click handle of the synthetic antigen; and
   sequencing each compound selected to obtain the corresponding peptide sequence of each compound selected, wherein each compound selected is capable of being used as a capture agent or for incorporation into a capture agent for the target protein.

2. The method of claim 1, wherein the compound library is a cyclic peptide library.

3. The method of claim 1, wherein the synthetic antigen is not subjected to a pegylation reaction and is not a pegylation product.

4. The method of claim 1, further comprising the step of labeling the synthetic antigen to allow for its detection after the step of incubating the synthetic antigen composition together with the at least a portion of the compound library.

5. The method of claim 1, wherein a plurality of compounds from the compound library are selected, wherein each compound selected has a corresponding peptide sequence and binds to the synthetic antigen in such a way that the complementary click handle of the compound will simultaneously bind the click handle of the synthetic antigen, and wherein the corresponding peptide sequence for each compound selected is different from the corresponding peptide sequence for every other compound selected.

6. The method of claim 5, further comprising the step of forming a construct comprising one or more arms, each of the arms incorporating at least one of the compounds selected.

7. The method of claim 6, wherein the construct further comprises:
   a solid support; and
   at least one linker connecting the plurality of arms, directly or indirectly, to the solid support.

8. The method of claim 6, wherein the construct is a one-arm construct selected from the group consisting of constructs having the following structure:

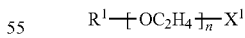

wherein $R^1$ is selected from the group consisting of H, OH, $NH_2$, $—CONH_2$, COOH, $OC_2H_5$, a solid support, a detection label, a linker connected to a solid support, and a linker connected to a detection label, and wherein $X^1$ is chosen from the library compounds selected based at least on their simultaneous attachment to the target protein and to one of its click handles, and salts, PEGylation products, tautomers, prodrugs, and stereoisomers, including enantiomers, thereof, wherein the integer n is greater than or equal to 1.

9. The method of claim 6, wherein the construct is a multi-arm

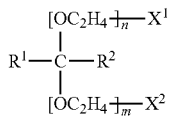

construct selected from the group consisting of constructs having the following structure:
wherein $R^1$ is selected from the group consisting of H, OH, $NH_2$, —$CONH_2$, COOH, $OC_2H_5$, $(OC_2H_4)_k$—OH, $(OC_2H_4)_k$—$NH_2$, $(OC_2H_4)_k$—$CONH_2$, $(OC_2H_4)_k$—COOH, $(OC_2H_4)_k$—$OC_2H_5$, $(OC_2H_4)_k$—$X^4$, a solid support, a detection label, a linker connected to a solid support, and a linker connected to a detection label, wherein $R^2$ is selected from the group consisting of H, OH, $NH_2$, —$CONH_2$, COOH, $OC_2H_5$, $(OC_2H_4)_k$—OH, $(OC_2H_4)_k$—$NH_2$, $(OC_2H_4)_k$—$CONH_2$, $(OC_2H_4)_k$—COOH, $(OC_2H_4)_k$—$OC_2H_5$, and $(OC_2H_4)_h$—$X^3$, wherein n, m, k, and h are integers that are equal to or greater than one, and wherein $X^1$, $X^2$, $X^3$, and $X^4$ are chosen from the compounds selected, and
salts, PEGylation products, tautomers, prodrugs, and stereoisomers, including enantiomers, thereof.

10. The method of claim 6, wherein the construct is a multi-arm construct selected from the group consisting of constructs having the following structure:

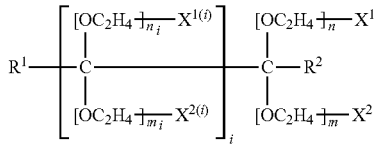

wherein $R^1$ is selected from the group consisting of H, OH, $NH_2$, —$CONH_2$, COOH, $OC_2H_5$, $(OC_2H_4)_k$—OH, $(OC_2H_4)_k$—$NH_2$, $(OC_2H_4)_k$—$CONH_2$, $(OC_2H_4)_k$—COOH, $(OC_2H_4)_k$—$OC_2H_5$, $(OC_2H_4)_k$—$X^4$, a solid support, a detection label, a linker connected to a solid support, and a linker connected to a detection label, wherein $R^2$ is selected from the group consisting of H, OH, $NH_2$, —$CONH_2$, COOH, $OC_2H_5$, $(OC_2H_4)_k$—OH, $(OC_2H_4)_k$—$NH_2$, $(OC_2H_4)_k$—$CONH_2$, $(OC_2H_4)_k$—COOH, $(OC_2H_4)_k$—$OC_2H_5$, and $(OC_2H_4)_h$—$X^3$, wherein i, n, m, $n_i$, $m_i$, k, and h are integers that are equal to or greater than one, and wherein $X^1$, $X^2$, $X^{1(i)}$, $X^{2(i)}$, $X^3$, and $X^4$ are chosen from the compounds selected, and
salts, tautomers, PEGylation products, prodrugs, and stereoisomers, including enantiomers, thereof.

11. The method of claim 6, wherein the construct is a multi-arm

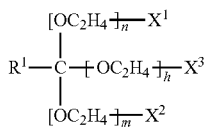

construct selected from the group consisting of constructs having the following structure:

wherein $R^1$ is selected from the group consisting of H, OH, $NH_2$, —$CONH_2$, COOH, $OC_2H_5$, $(OC_2H_4)_k$—OH, $(OC_2H_4)_k$—$NH_2$, $(OC_2H_4)_k$—$CONH_2$, $(OC_2H_4)_k$—COOH, $(OC_2H_4)_k$—$OC_2H_5$, $(OC_2H_4)_k$—$X^4$, a solid support, a detection label, a linker connected to a solid support, and a linker connected to a detection label, wherein n, m, k, and h are integers that are equal to or greater than one, and wherein $X^1$, $X^2$, $X^3$, and $X^4$ are chosen from the compounds selected, and
salts, tautomers, PEGylation products, prodrugs, and stereoisomers, including enantiomers, thereof.

12. The method of claim 7, wherein the solid support is selected from the group consisting of beads, multi-well ELISA plates, and BRAP chips.

13. The method of claim 1, wherein $X^1$, $X^2$, $X^3$, and $X^4$ each comprise a variable portion consisting of the corresponding polypeptide of each of $X^1$, $X^2$, $X^3$, and $X^4$, and wherein the corresponding polypeptide of each of $X^1$, $X^2$, $X^3$, and $X^4$ is selected from the group consisting of Tryptophan-Isoleucine-Tyrosine-Tyrosine-Isoleucine (SEQ ID NO: 1), Tyrosine-Tryptophan-Histidine-Tryptophan-Serine (SEQ ID NO: 2), Isoleucine-Tyrosine-Leucine-Arginine-Tyrosine (SEQ ID NO: 3), Phenylalanine-Tryptophan-Glutamine-Isoleucine-Leucine (SEQ ID NO: 4), and the D-amino acid versions of these sequences.

14. The method of claim 1, wherein the target protein is a protein from a pathogen.

15. The method of claim 1, wherein the target protein is the CHIKV E2 protein.

16. A method for developing a capture agent for identification of a target protein, the method comprising:
providing a target protein comprising a whole protein and having one or more N-terminii, each of the N-terminii comprising one or more free amines;
modifying the whole target protein by one or more chemical reactions to attach a clickable group selected from the group consisting of an alkyne group and an azide group on at least one of the free amines on at least one of the N-terminii of the target protein to thereby form a synthetic antigen comprising the modified whole target protein and the attached clickable group(s) without having prior knowledge of the structure of the whole target protein;
providing a compound library of a plurality of library compounds, each of the library compounds comprising a macrocyclic peptide molecule and a clickable terminal group selected from the group consisting of an alkyne group and an azide group that is complementary to the attached clickable group(s) of the synthetic antigen;
incubating the at least a portion of the compound library together with a solution containing the synthetic antigen for a sufficient time so as to produce covalent triazole ring bonding between one or more molecules of the synthetic antigen and a corresponding number of the library compounds;
isolating a sub-set of the library compounds exhibiting covalent triazole ring bonding with the synthetic antigen;
performing an anti-screening on the isolated sub-set of the library compounds by incubating the isolated sub-set with a complex biological solution;
selecting as candidate compounds one or more of the isolated sub-set of library compounds that exhibited the lowest levels of interaction with the complex biological solution;

sequencing at least a variable portion of each of the selected candidate compounds to obtain the corresponding peptide sequence of the variable portion thereof;

forming one or more construct molecules, each of the one or more construct molecules comprising one or more polymer arms incorporating the corresponding peptide sequence of at least one of the selected candidate compounds and an assay tag suitable for an immune-assaying technique that produces assaying results;

assaying the target protein, with the immuno-assaying technique, using the construct molecules;

identifying, from the assaying results, one or more construct molecules that have sufficient affinity and selectivity for the target protein to be suitable for use as the capture agent; and identifying, from the assaying results, values of one or more parameters of assaying that correlate with the corresponding peptide sequence of each of the selected candidate compounds.

17. A method for identification of the presence of the target protein using the capture agent developed using the method of claim 16, the identification method comprising:
obtaining a sample to screen for the target protein;

assaying, with the same immuno-assaying technique, the sample using the capture agent; and identifying, from the values for the one or more parameters of assaying obtained from the assaying results, whether the sample comprises the target protein.

18. A method for inhibiting infection of a host by a pathogen associated with the target protein using the corresponding peptide sequence of at least one of the selected candidate compounds developed using the method of claim 16, the inhibiting method comprising:

administering a pharmaceutical formulation comprising a pharmaceutically acceptable construct molecule comprising one or more polymer arms incorporating the corresponding peptide sequence of at least one of the selected candidate compounds identical to that used in the construct molecule found suitable for use as a capture agent in accordance with the method of claim 17 to the host, wherein the corresponding peptide sequence interacts with the target protein in the host.

19. The method of claim 16, wherein the target protein comprises the Chikungunya virus (CHIKV) E2 surface protein.

20. The method of claim 19, wherein the corresponding peptide sequence of the selected candidate compounds is selected from the group consisting of Tryptophan-Isoleucine-Tyrosine-Tyrosine-Isoleucine (SEQ ID NO: 1), Tyrosine-Tryptophan-Histidine-Tryptophan-Serine (SEQ ID NO: 2), Isoleucine-Tyrosine-Leucine-Arginine-Tyrosine (SEQ ID NO: 3), Phenylalanine-Tryptophan-Glutamine-Isoleucine-Leucine (SEQ ID NO: 4), and the D-amino acid versions of these sequences.

21. The method of claim 16 further comprising:

performing a pre-clear screening of the compound library by incubating the library peptide molecules with one or more substances selected from the group consisting of an antibody of the target protein and one or more assay tagging molecules; and subsequently removing those library compounds which bind to the one or more substances.

22. The method of claim 16, wherein the anti-screening step further comprises:

ranking the isolated sub-set peptide molecule that interacted with the complex biological solution in order of least interactivity.

23. The method of claim 16, wherein the assay tag is selected from the group consisting of polymer-based beads, dyed polymer-based beads, fluorescent beads, quantum dots, nanoparticles, magnetic beads, surfaces selected from metals, silicon, graphene, and polymeric, detection labels, and fluorophores.

24. The method of claim 16, wherein the immune-assaying technique is selected from the group consisting of enzyme-linked immunoassays, surface plasmon resonance-based immunoassays, lateral flow immunoassays, electrochemical-based immunoassays, paper-based immunoassays, fluorescence-based immunoassays, DNA-based immunoassays, radioactive-based immunoassays, label-free immunoassays, chemiluminescence-based immunoassays, acoustic wave-based immunoassays, interferometry-based immunoassays, nanomaterial- and micromaterial-based immunoassays, microcantilever-based immunoassays, optical-based immunoassays, magnetic-based immunoassays, microarray immunoassays, quartz crystal microbalance-based immunoassays, Lab-on-a-Chip (LOC) immunoassays, smartphone-based immunoassays, and wearable immunoassays.

25. The method of claim 1, wherein the whole target protein has one or more N-terminii, each of the N-terminii comprising one or more free amines and/or lysine amino acids, and modifying the whole target protein comprises:

converting the one or more free amines and/or lysine amino acids to the group consisting of an alkyne group and an azide group.

26. The method of claim 1, wherein said modifying of the whole target protein does not require prior knowledge of the amino acid sequence in whole or in part of the whole target protein.

* * * * *

SEQUENCE LISTING

```
<160> NUMBER OF SEQ ID NOS: 4

<210> SEQ ID NO 1
<211> LENGTH: 5
<212> TYPE: PRT
<213> ORGANISM: Artificial Sequence
<220> FEATURE:
<223> OTHER INFORMATION: Synthetic construct

<400> SEQUENCE: 1

Trp Ile Tyr Tyr Ile
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic construct

<400> SEQUENCE: 2
```

```
Tyr Trp His Trp Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic construct

<400> SEQUENCE: 3

Ile Tyr Leu Arg Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic construct

<400> SEQUENCE: 4

Phe Trp Gln Ile Leu
1               5
```